United States Patent [19]

Malecki et al.

[11] Patent Number: 5,626,607

[45] Date of Patent: *May 6, 1997

[54] CLAMP ASSEMBLY AND METHOD OF USE

[75] Inventors: William W. Malecki; Wesley D. Sterman, both of San Francisco; Hanson S. Gifford, III, Woodside; Scott H. Miller, Sunnyvale, all of Calif.

[73] Assignee: Heartport, Inc., Redwood City, Calif.

[ * ] Notice: The term of this patent shall not extend beyond the expiration date of Pat. No. 5,425,705.

[21] Appl. No.: 595,568

[22] Filed: Feb. 1, 1996

Related U.S. Application Data

[63] Continuation-in-part of Ser. No. 567,996, Dec. 4, 1995, which is a continuation-in-part of Ser. No. 415,273, Apr. 3, 1995, Pat. No. 5,536,251.

[51] Int. Cl.$^6$ ...................................... A61B 17/28
[52] U.S. Cl. ........................... 606/205; 606/206; 606/211
[58] Field of Search ...................... 604/19, 27–28, 604/36, 93, 115–117, 164, 56, 51–53, 44, 4; 606/205–211; 128/751

[56] References Cited

U.S. PATENT DOCUMENTS

| | | |
|---|---|---|
| 3,503,397 | 3/1970 | Fogarty et al. . |
| 3,503,398 | 3/1970 | Fogarty et al. . |
| 4,318,401 | 3/1982 | Zimmerman . |
| 4,531,935 | 7/1985 | Berryessa . |
| 4,531,936 | 7/1985 | Gordon . |
| 4,568,330 | 2/1986 | Kujawski et al. . |
| 4,610,661 | 9/1986 | Possis et al. . |
| 5,013,296 | 5/1991 | Buckberg et al. . |
| 5,133,724 | 7/1992 | Wilson et al. . |
| 5,156,609 | 10/1992 | Nakao et al. . |
| 5,167,628 | 12/1992 | Boyles . |
| 5,211,655 | 5/1993 | Hasson . |
| 5,224,931 | 7/1993 | Kumar . |
| 5,290,294 | 3/1994 | Cox et al. . |
| 5,330,498 | 7/1994 | Hill . |
| 5,425,705 | 6/1995 | Evard . |
| 5,454,826 | 10/1995 | Ueda . |

OTHER PUBLICATIONS

"DynaBite Biopsy Forceps, " Portlyn Medical Products Division, Product Information, 1993, 2 pages.

"DynaBite™ Biopsy Forceps," Portlyn Medical Products Division, New Product Announcement for 3.3mm G.I. Biopsy Forceps.

"DynaBite™ Biopsy Forceps," Portlyn Medical Products Division, New Product Announcement for 1.0mm G.I. and Pulmonary Biopsy Forceps.

Miltex M. Surgical Instruments "Thoracic and Cardiovascular Instruments," Miltex Instrument Company, Inc. 1986, p. 319.

Pilling Surgical Instruments "Aortic Calims," 1993, pp. 349–351.

*Primary Examiner*—Randall L. Green
*Assistant Examiner*—Perry E. Van Over
*Attorney, Agent, or Firm*—Townsend and Townsend and Crew LLP

[57] ABSTRACT

A clamp for clamping a body structure in a patient. The clamp includes a flexible cable housed within a sheath. The cable and sheath extend between a clamp and a handle. The cable actuator. The cable extends through a sheath which is anchored at the clamp and the actuator for actuating jaws from a proximal end of the clamp. A malleable positioner is provided for positioning the clamp about the body structure.

33 Claims, 30 Drawing Sheets

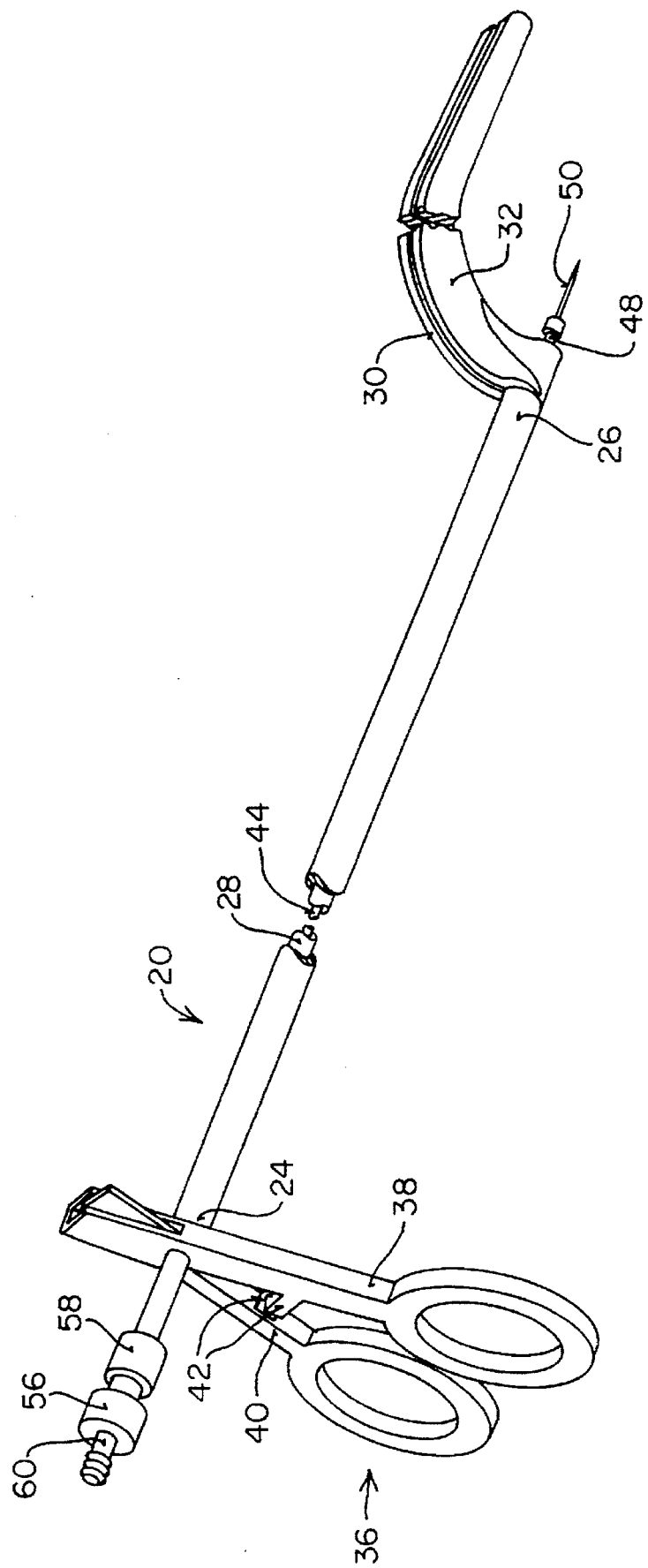
FIG_1

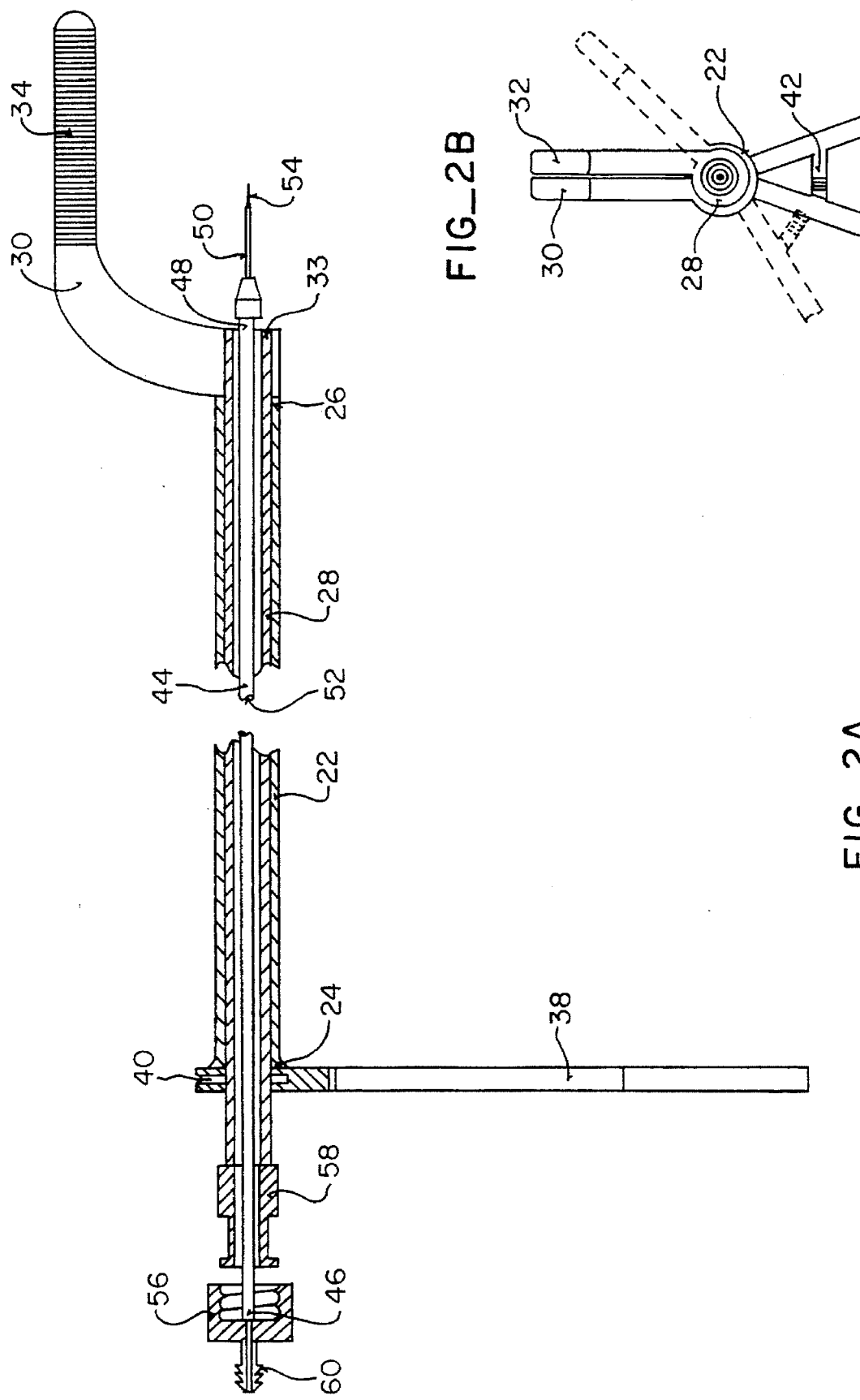

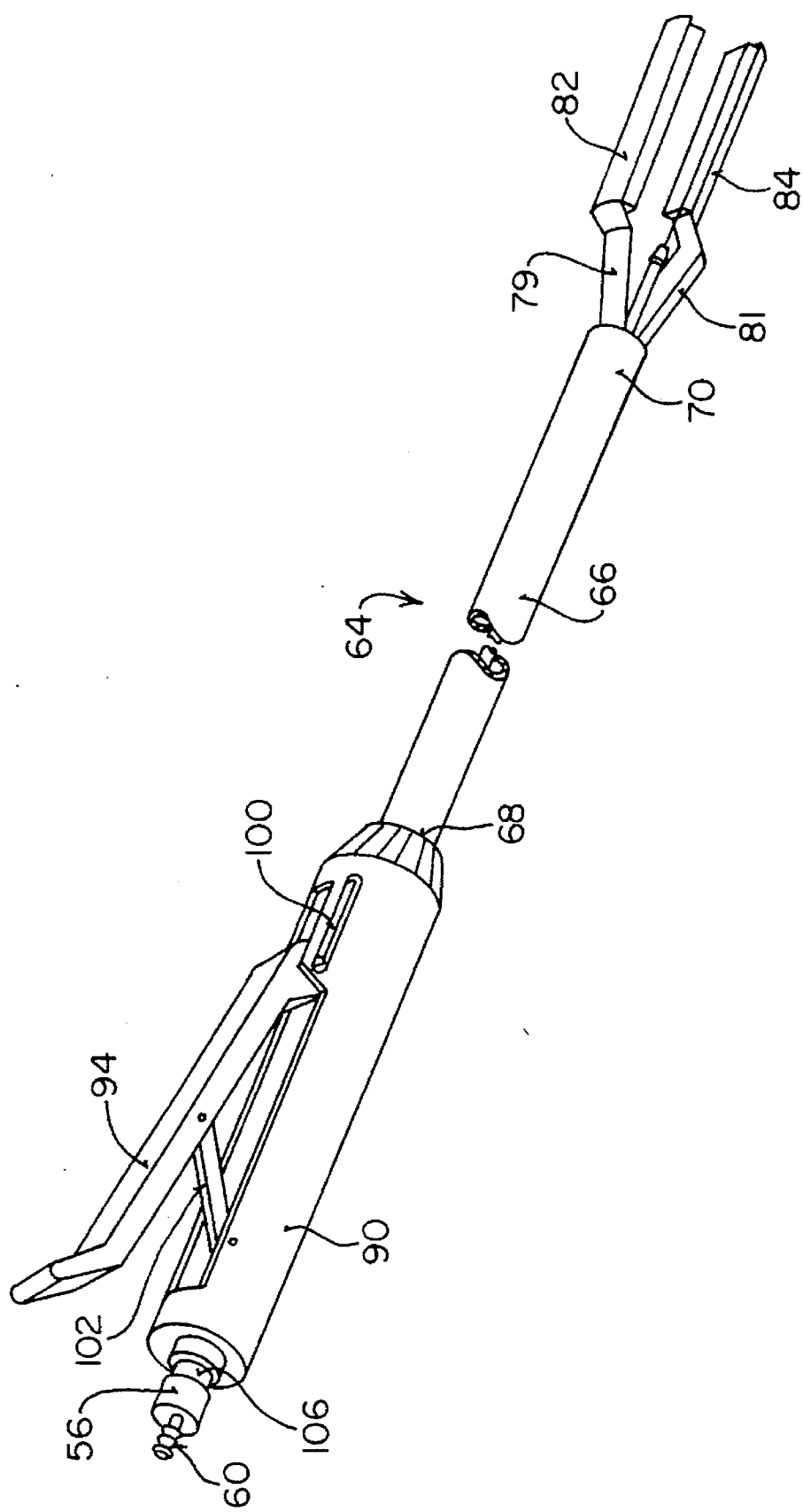
FIG_3

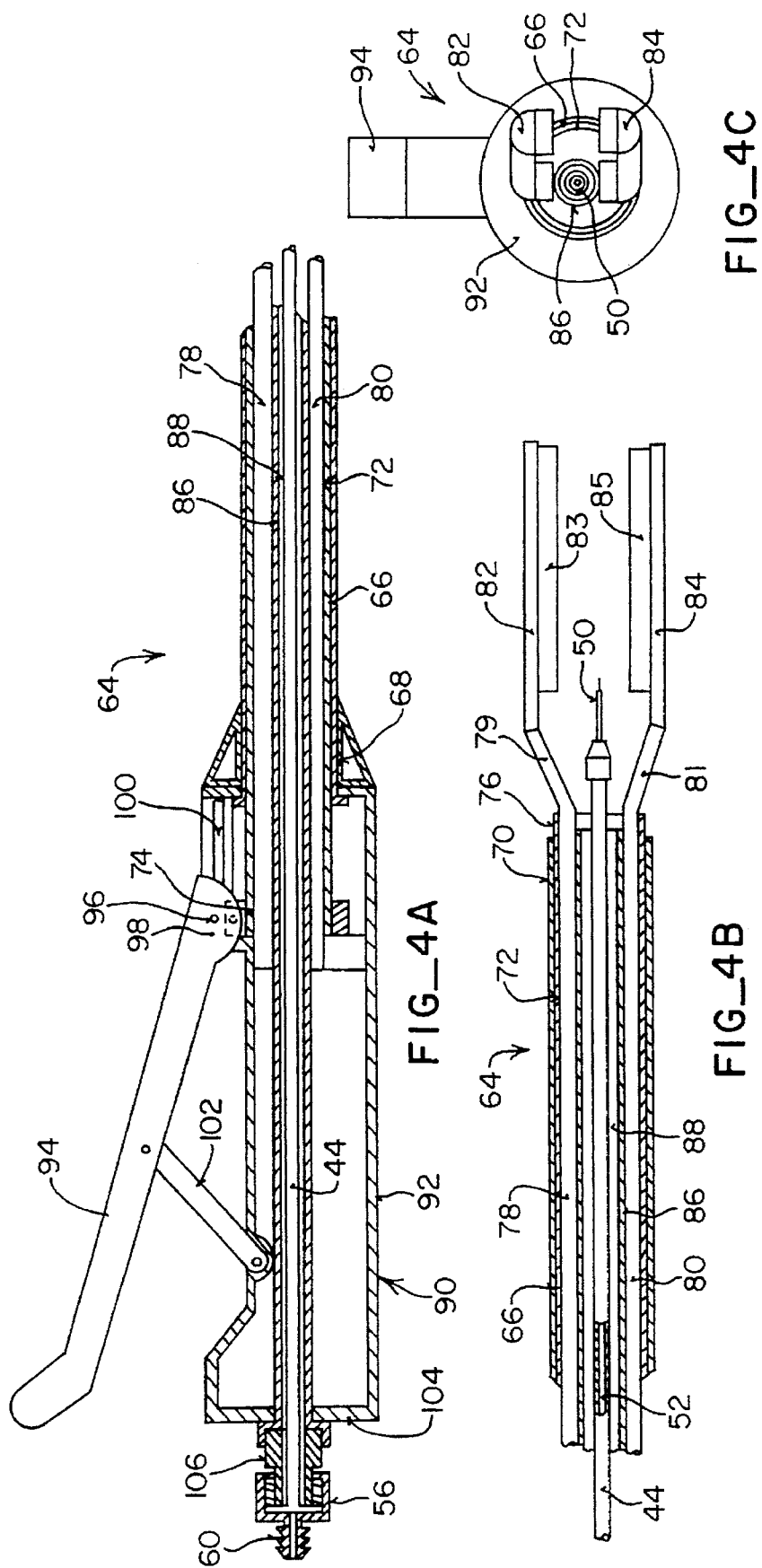

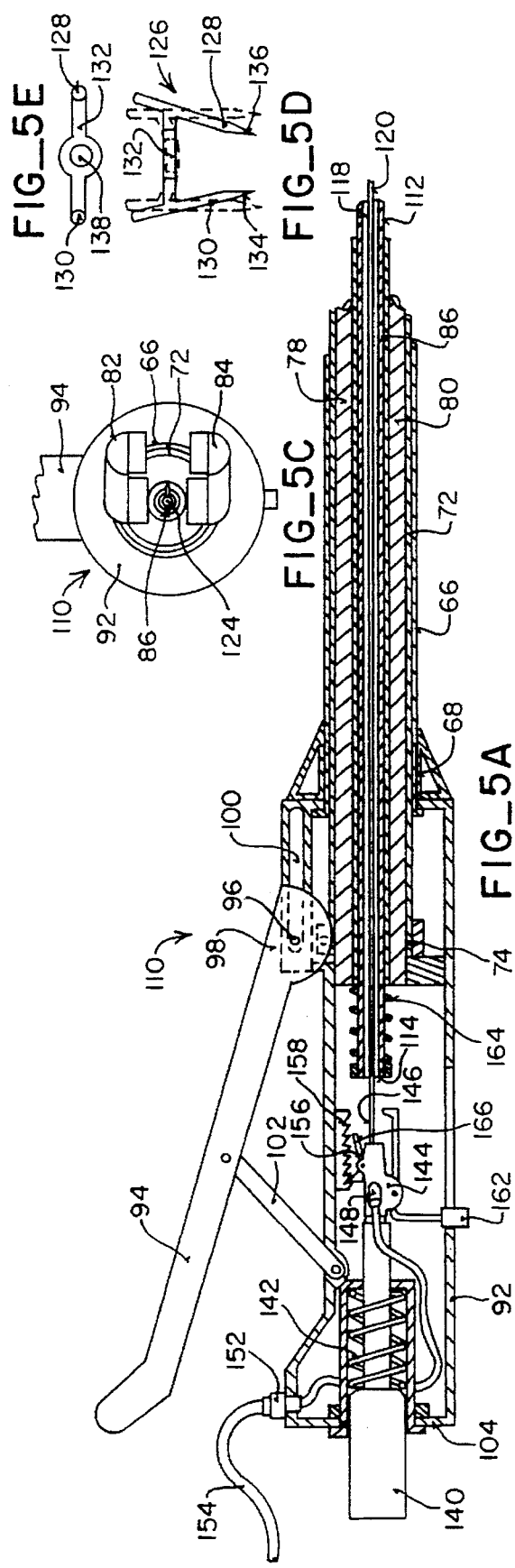
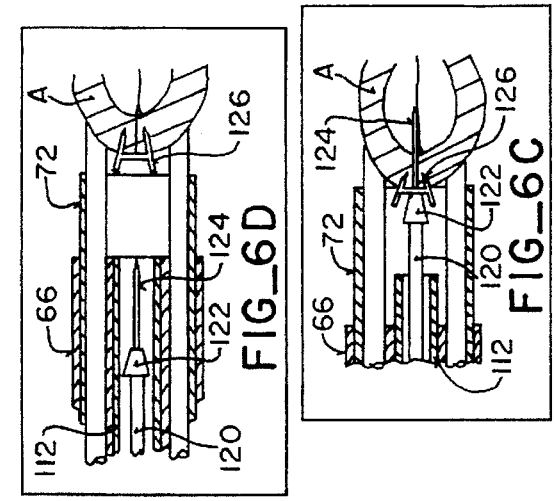
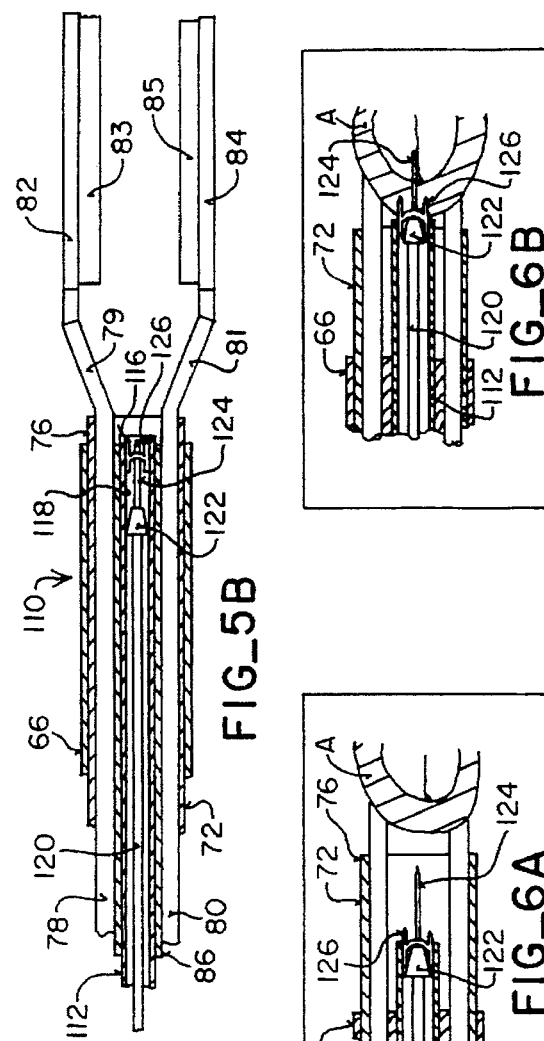
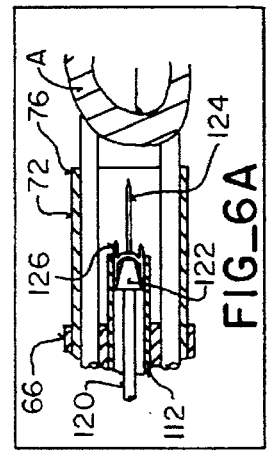

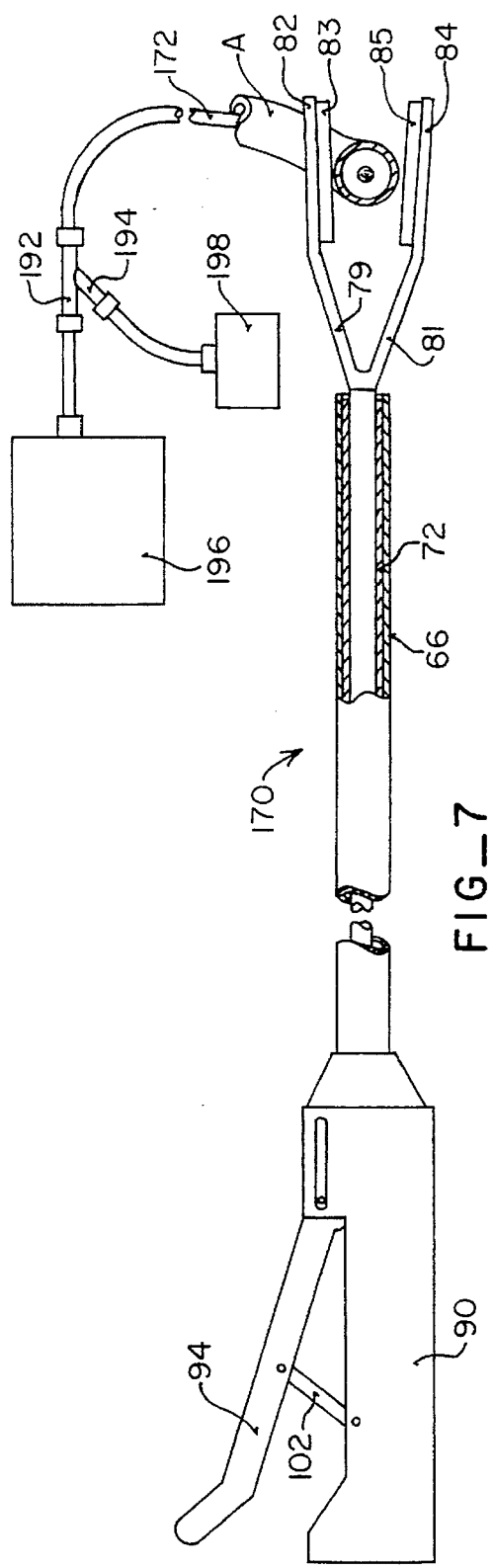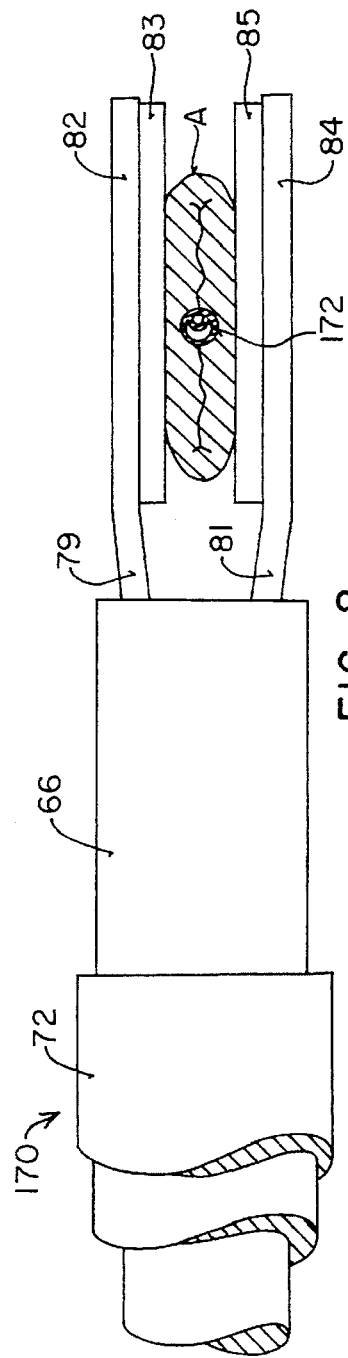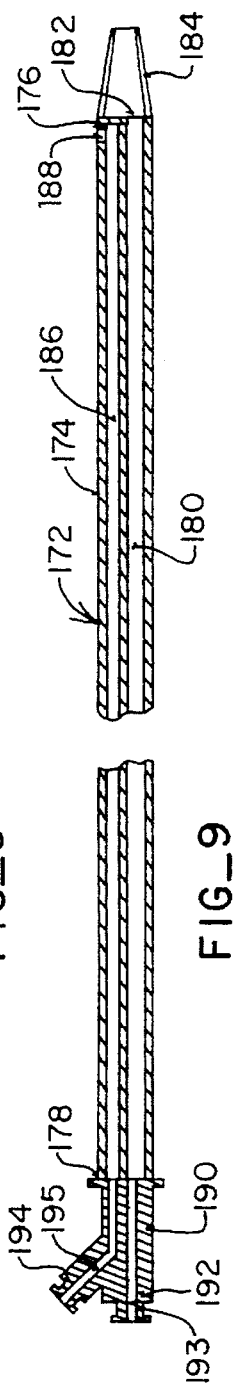

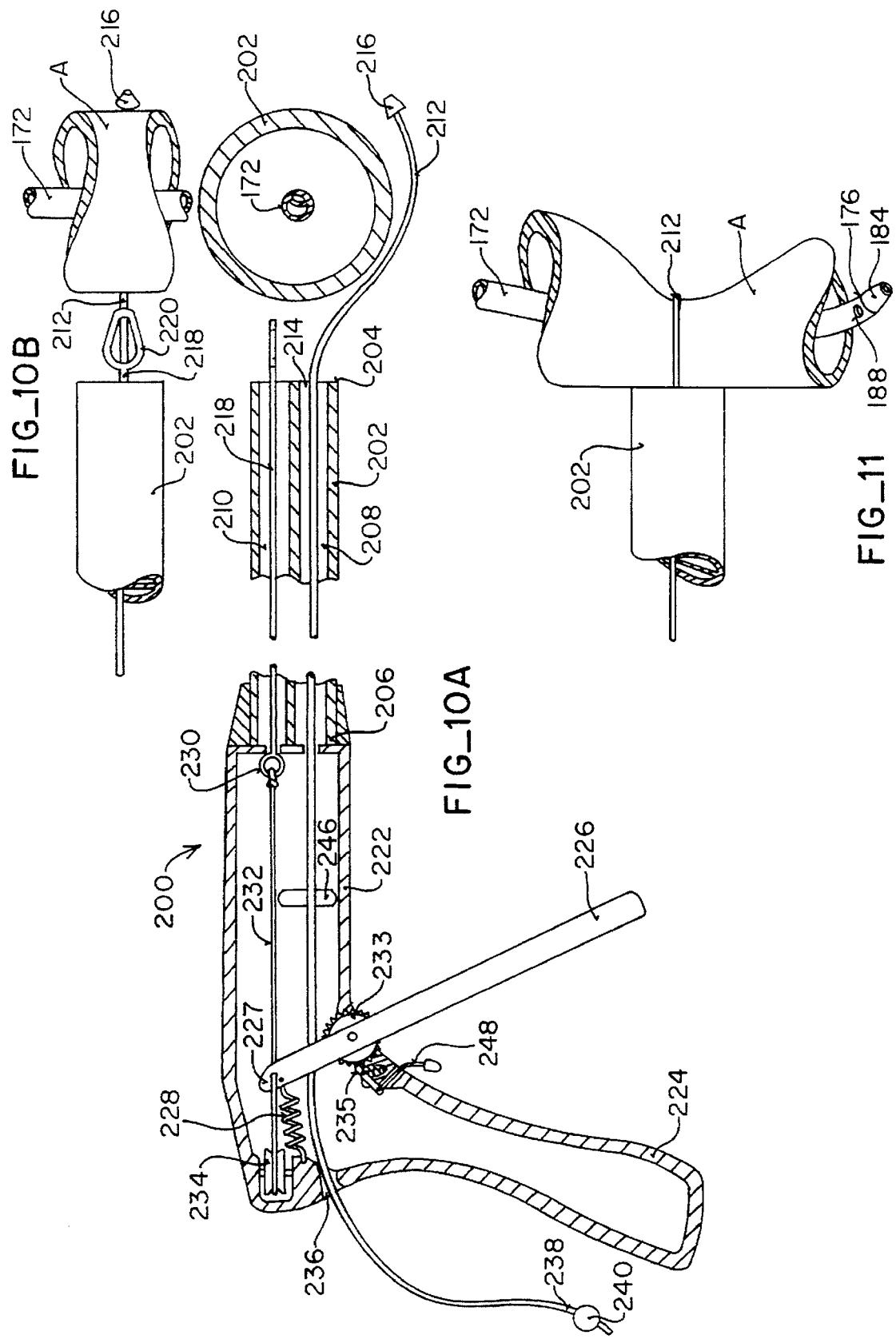

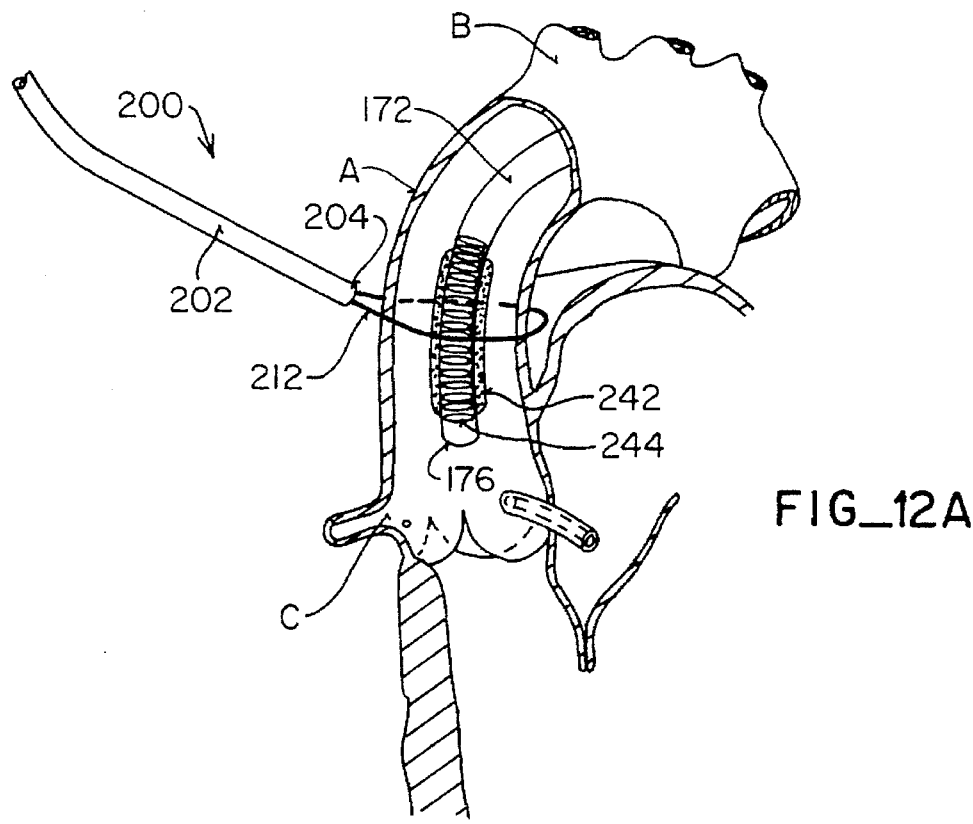
FIG_12A
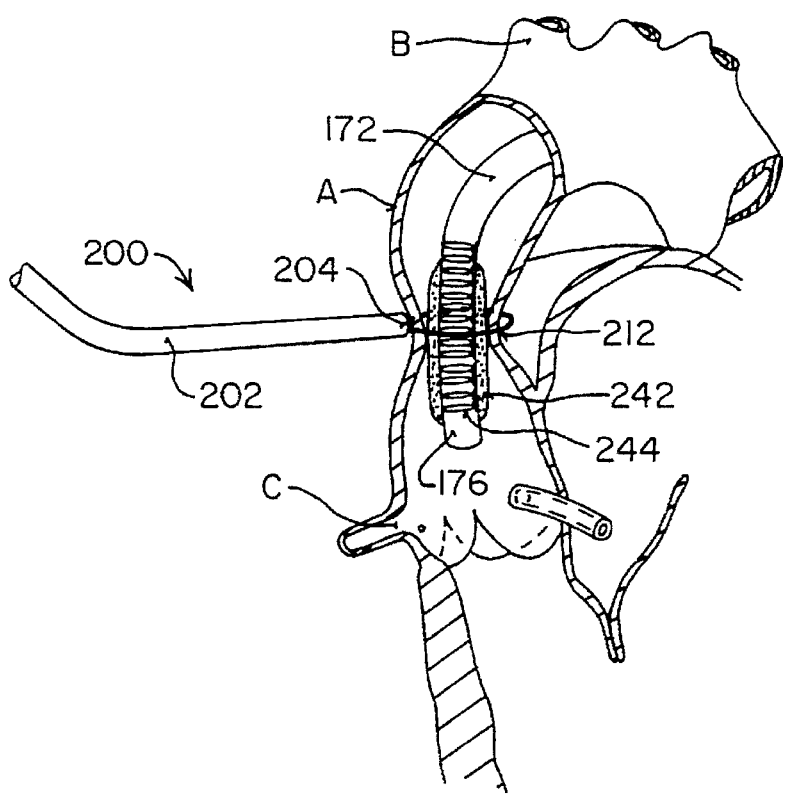
FIG_12B

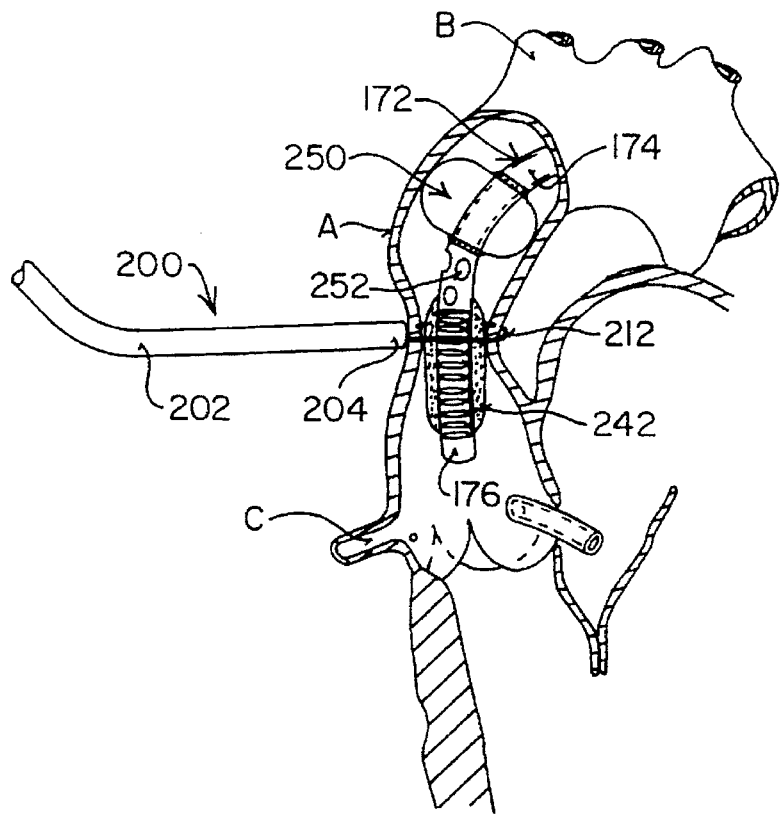
FIG_13
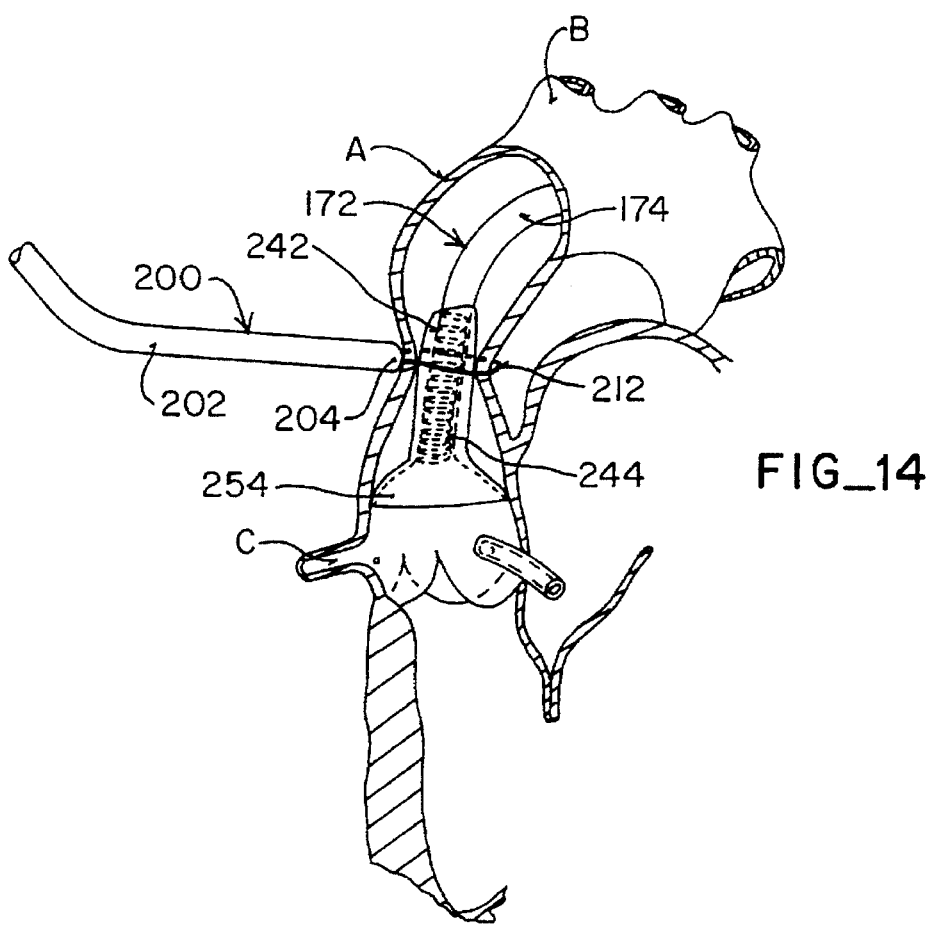
FIG_14

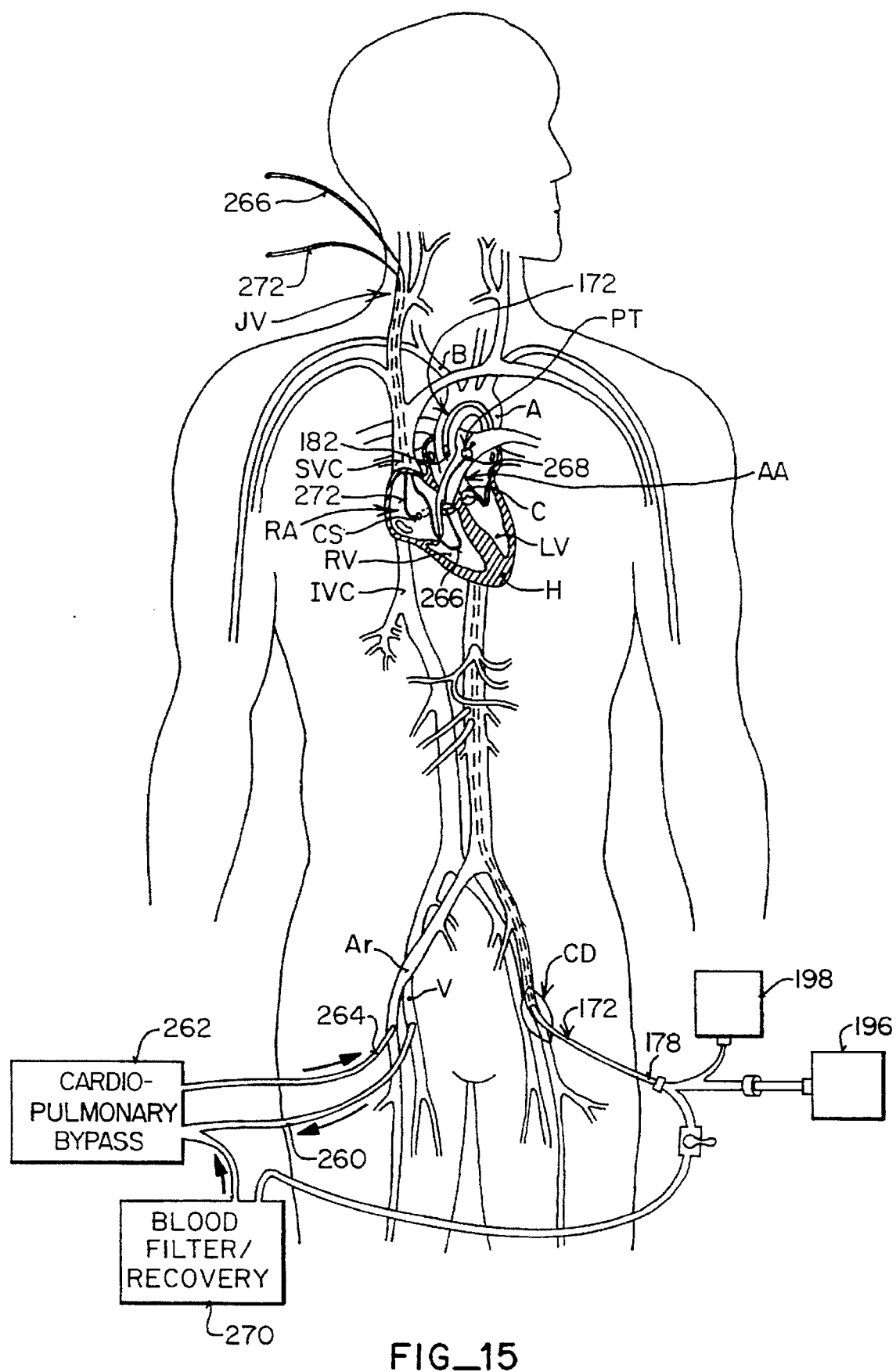
FIG_15

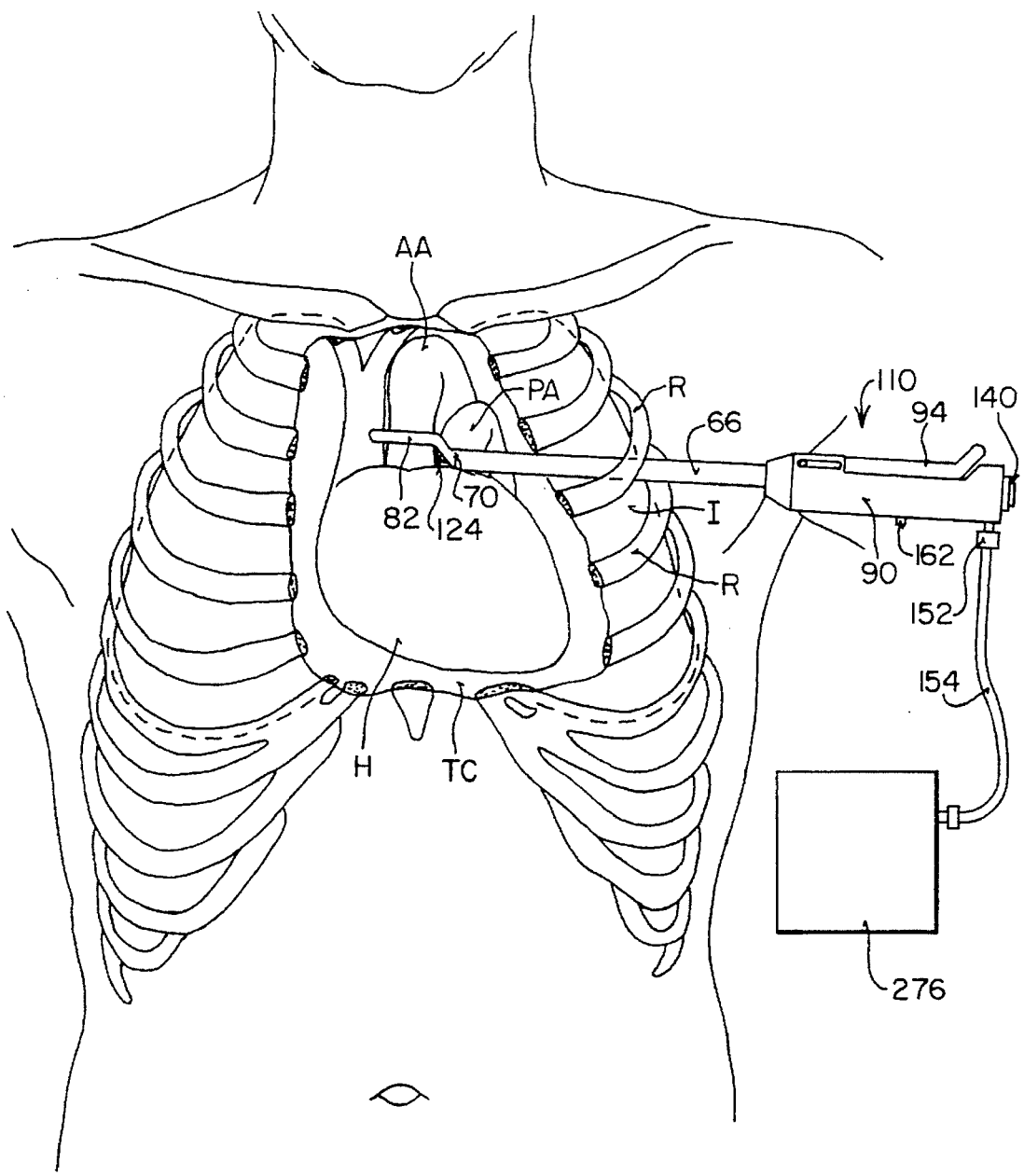
FIG_16

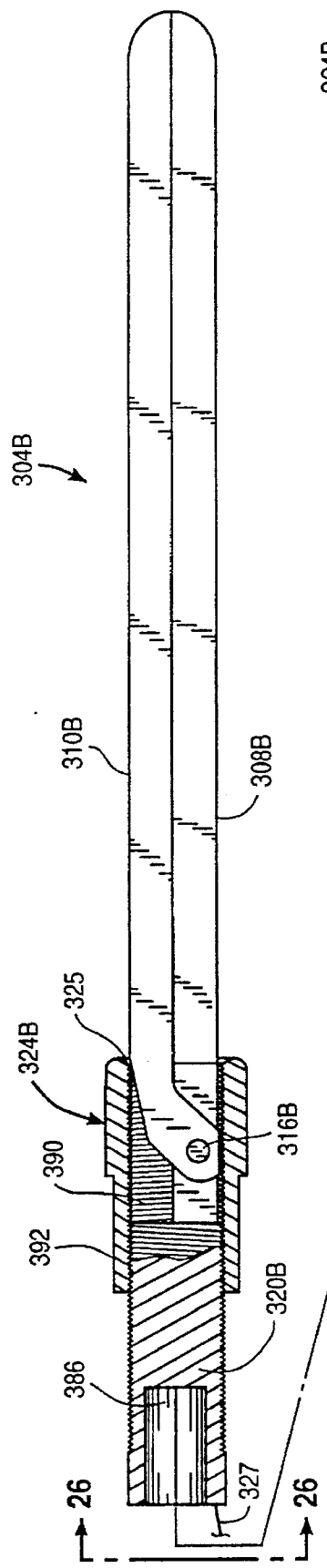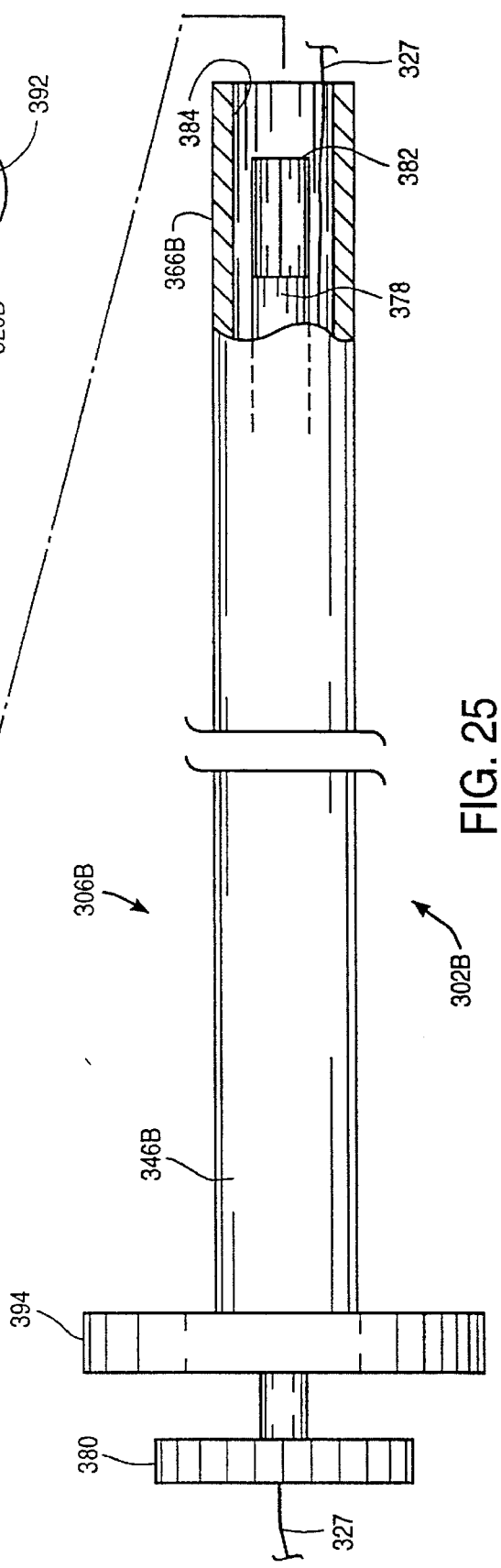
FIG. 26
FIG. 25

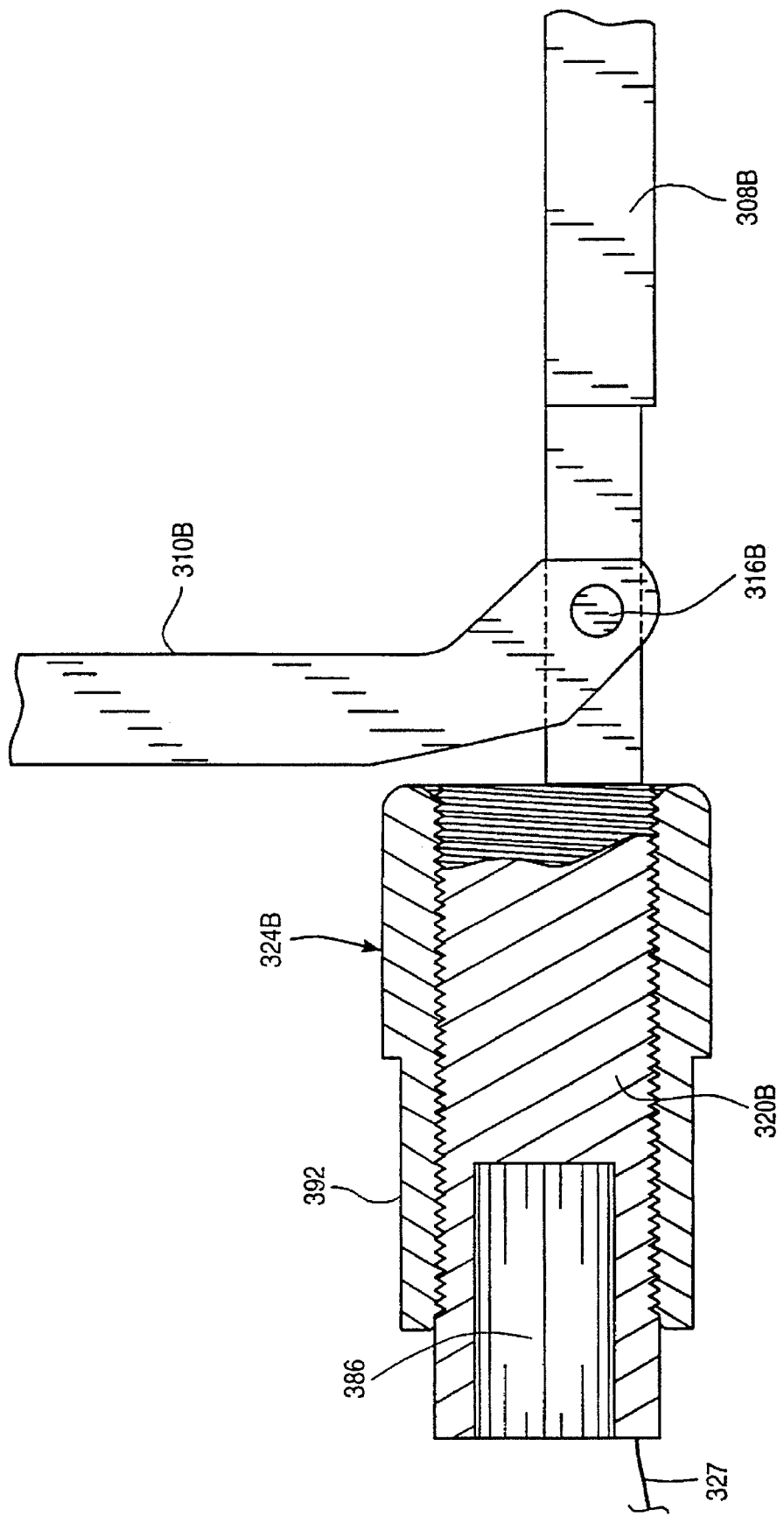

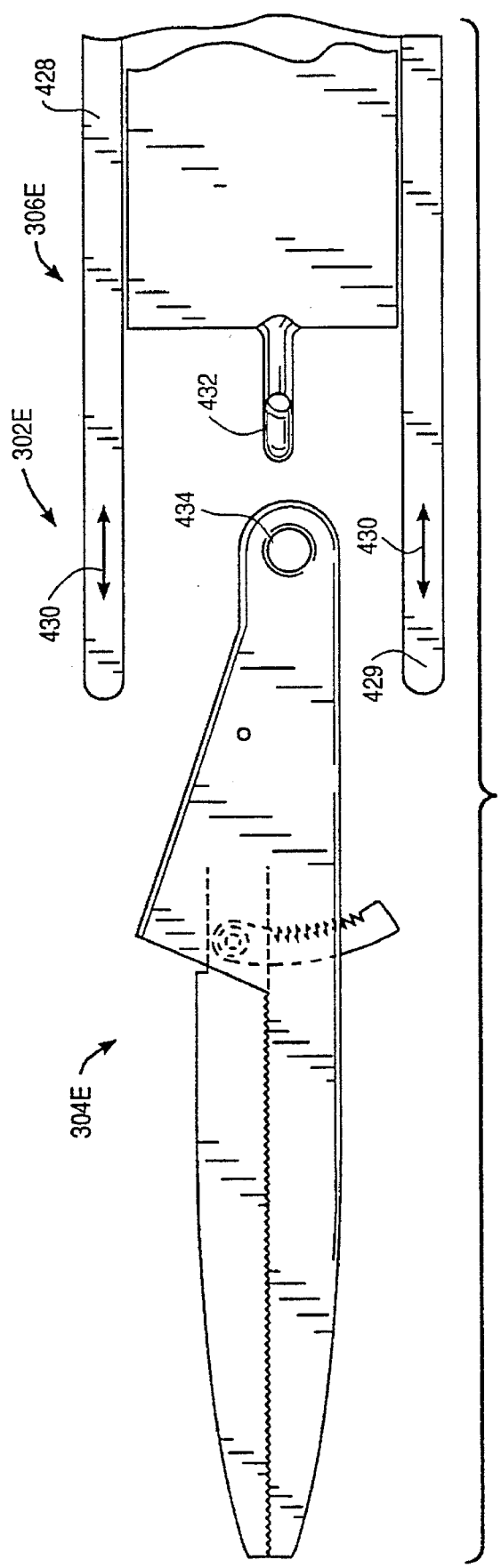
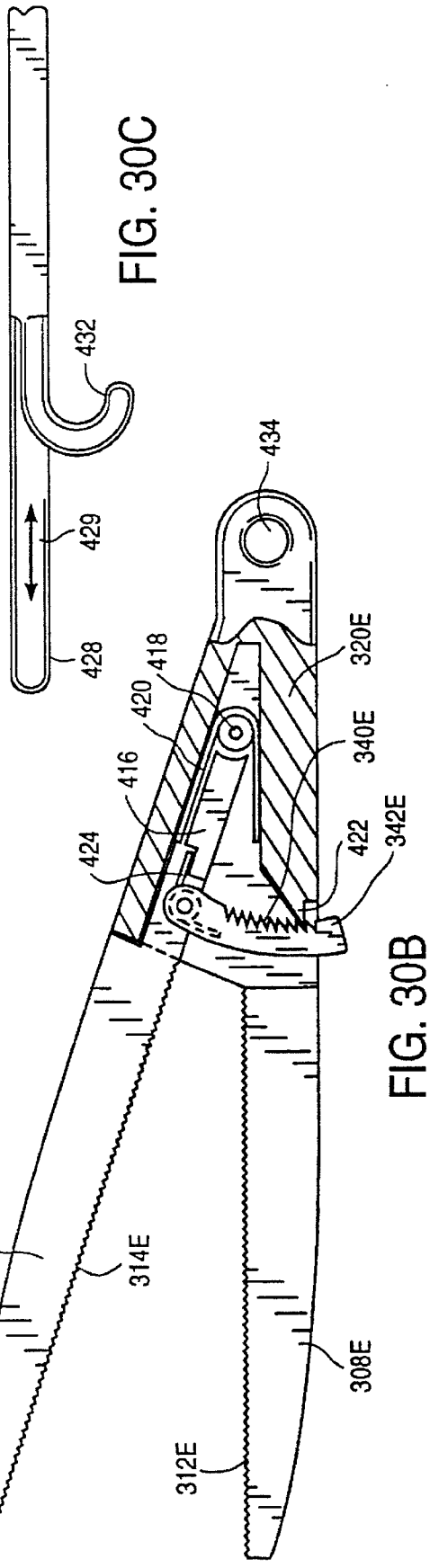
FIG. 30A
FIG. 30B
FIG. 30C

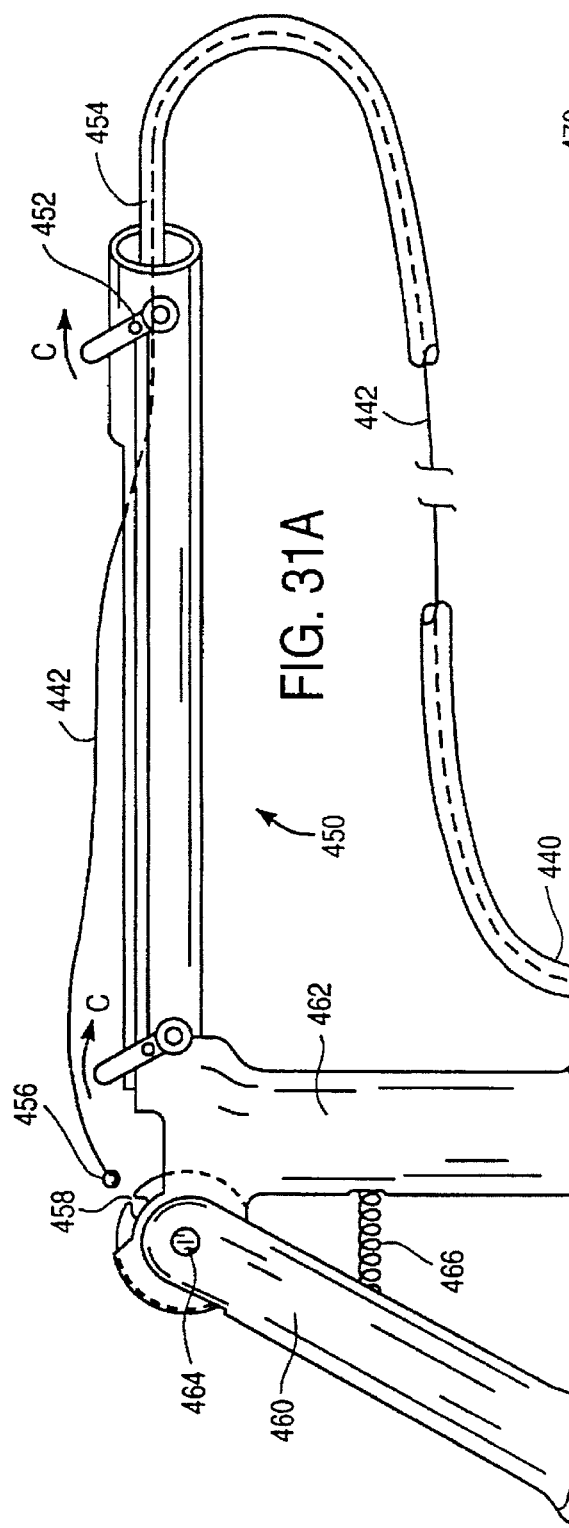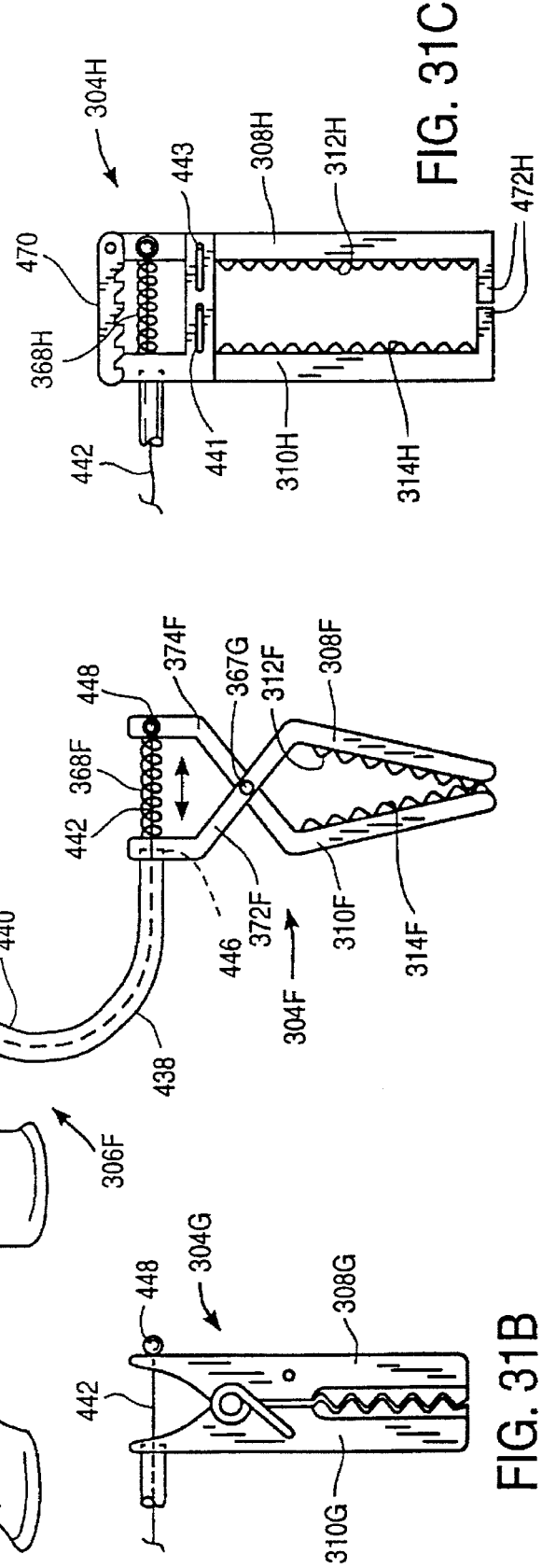

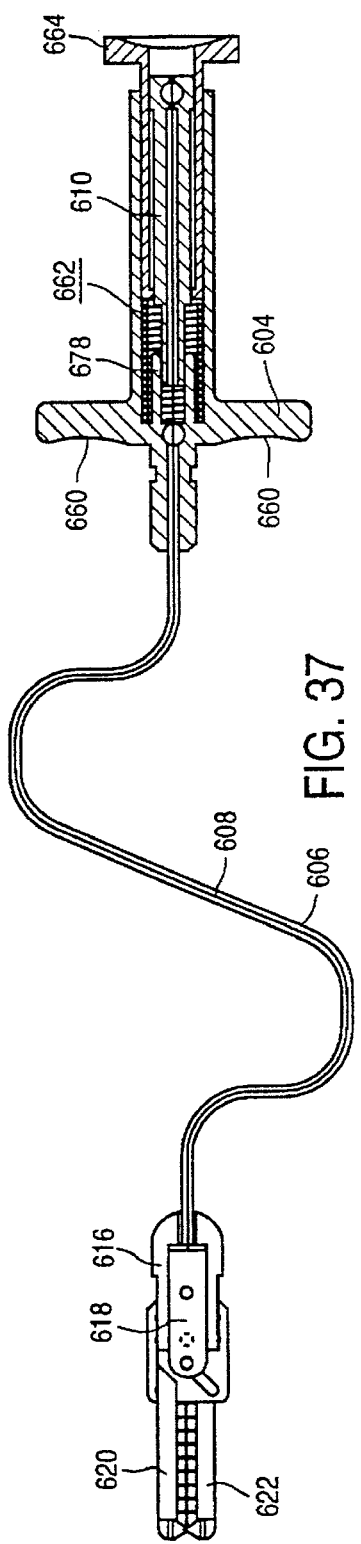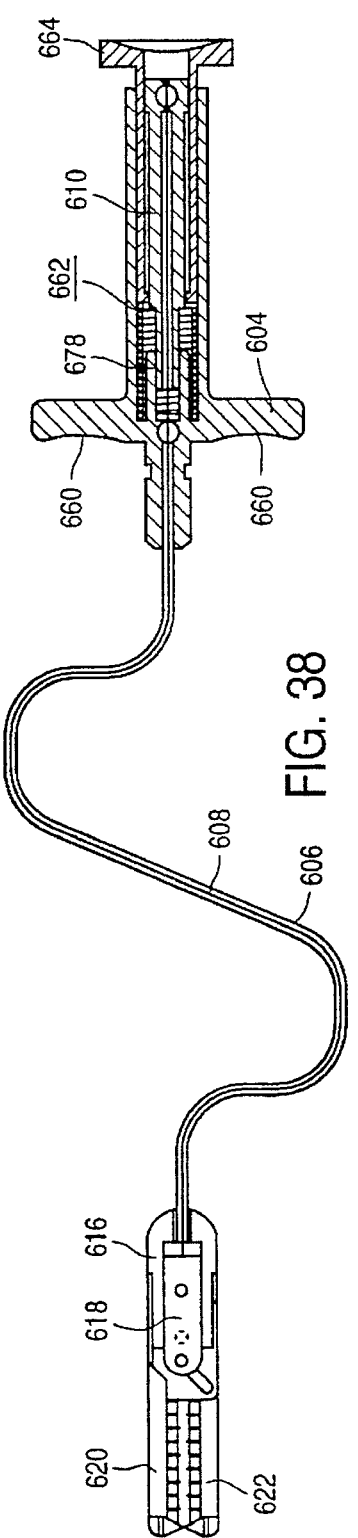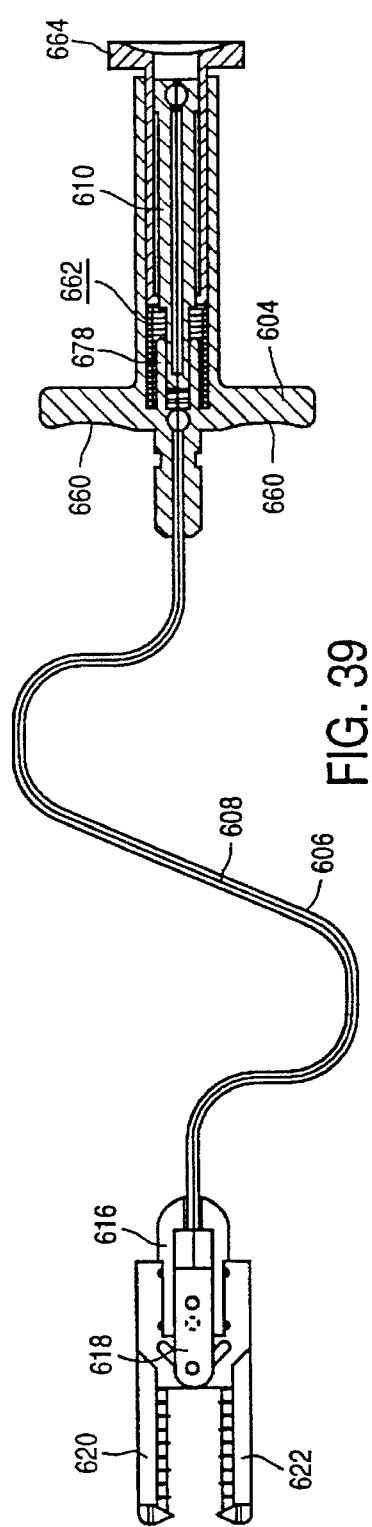

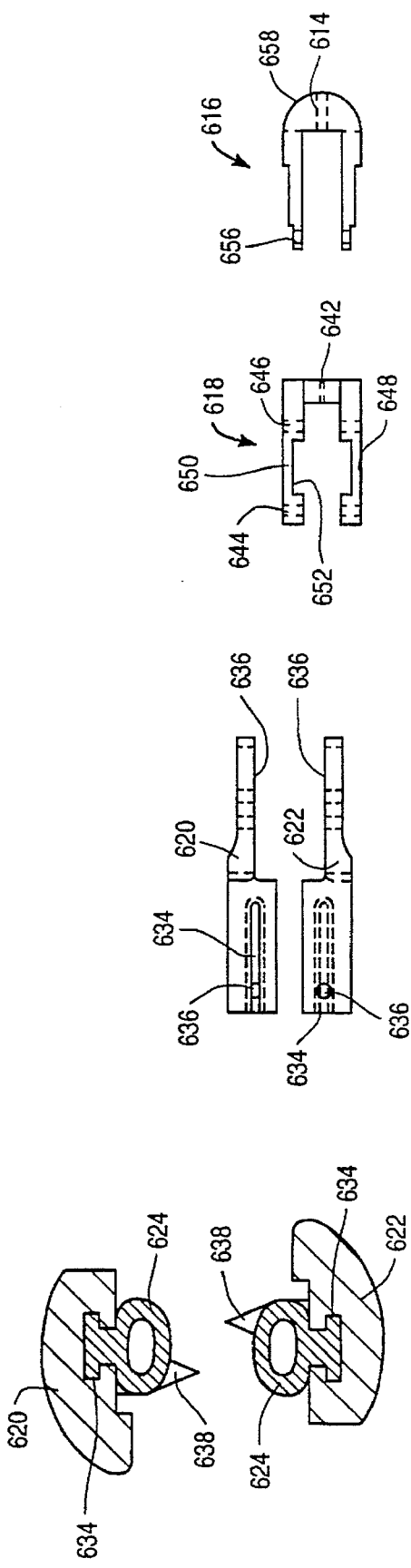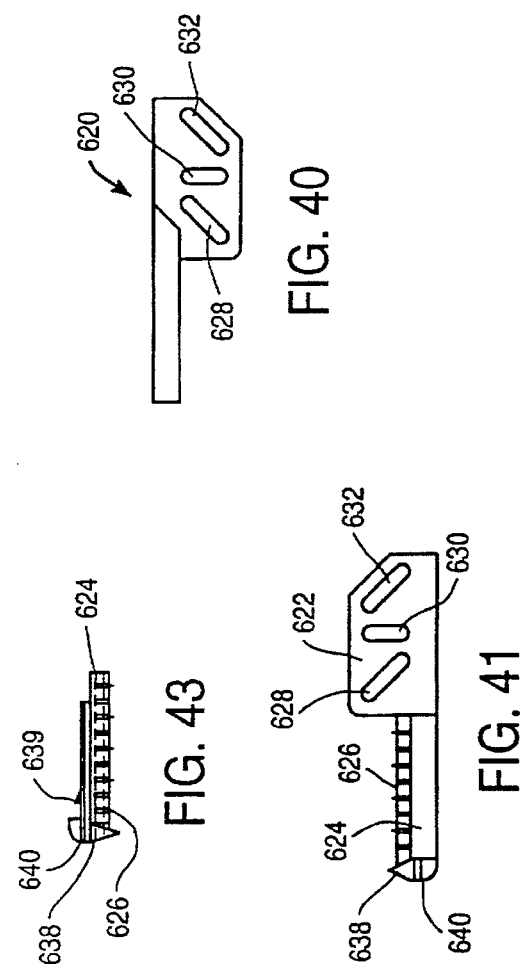

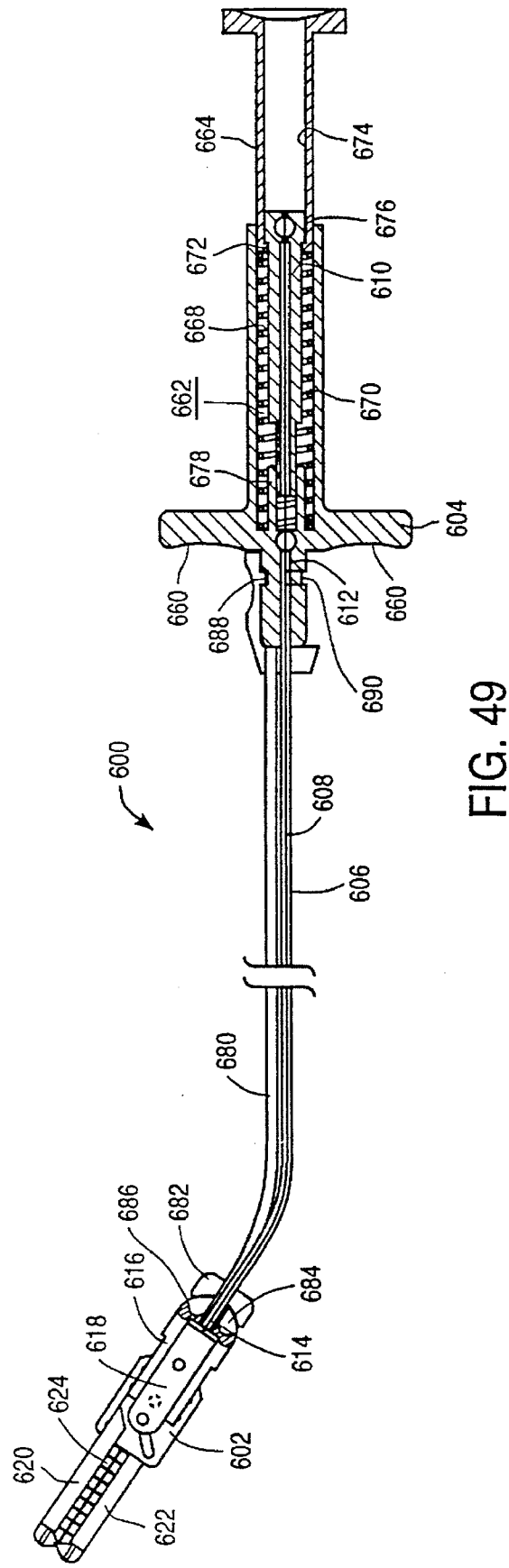

CLAMP ASSEMBLY AND METHOD OF USE

CROSS-REFERENCE TO RELATED APPLICATIONS

This application is a continuation-in-part of application of U.S. patent application Ser. No. 08/567,996, filed Dec. 4, 1995, by inventors Donlon, Stevens, Mueller, Daniel and Gifford, which is a continuation-in-part of application Ser. No. 08/415,273, filed Apr. 3, 1995, now U.S. Pat. No. 5,536,251 by inventors Philip C. Evard et al., and is related to commonly-assigned U.S. patent application Ser. No. 08/173,899, filed Dec. 27, 1993, now issued as U.S. Pat. No. 5,425,705, the complete disclosures of which are hereby incorporated by reference.

FIELD OF THE INVENTION

This invention relates to less-invasive surgical instruments for clamping hollow body structures. A specific application of the present invention is described in connection with less-invasive devices and methods which can be used for isolating the heart and coronary blood vessels from the remainder of the arterial system. Another specific application of the present invention is for clamping of the internal mammary artery for performing a coronary artery bypass procedure.

BACKGROUND OF THE INVENTION

Various cardiovascular, neurosurgical, pulmonary, and other interventional procedures, including coronary artery bypass grafting, heart valve repair and replacement, septal defect repair, pulmonary thrombectomy, removal of atrial myxoma, patent foramen oval closure, treatment of aneurysms, myocardial drilling, electrophysiological mapping and ablation, angioplasty, atherectomy, correction of congenital defects, and other interventional procedures may require general anesthesia, cardiopulmonary bypass, and arrest of cardiac function. In order to arrest cardiac function, the heart and coronary blood vessels must be isolated from the remainder of the circulatory system. This serves several purposes. First, such isolation facilitates infusion of cardioplegic fluid into the coronary arteries to perfuse the myocardium and paralyze the heart without allowing the cardioplegic fluid to be distributed elsewhere in the patient's circulatory system. Second, such isolation facilitates use of a cardiopulmonary bypass system to maintain circulation of oxygenated blood throughout the circulatory system while the heart is stopped without allowing such blood to reach the coronary arteries and resuscitate the heart. Third, in cardiac procedures, such isolation creates a working space into which the flow of blood and other fluids can be controlled or prevented so as to create an optimum surgical environment.

Circulatory isolation of the heart and coronary blood vessels is usually accomplished by placing a mechanical cross-clamp externally on the ascending aorta downstream of the ostia of the coronary arteries, but upstream of the brachiocephalic artery so that oxygenated blood from the cardiopulmonary bypass system reaches the arms, neck, head, and remainder of the body. Using conventional techniques, the sternum is cut longitudinally (a median sternotomy) thereby providing access between opposing halves of the anterior portion of the rib cage to the heart and other thoracic vessels and organs. Alternatively, a lateral thoracotomy is formed, wherein a large incision is made between two ribs and the ribs are retracted apart. A portion of one or more ribs may be permanently removed to optimize access.

Through this large opening in the chest, a cross-clamp is placed externally on the ascending aorta thereby isolating the heart and coronary arteries from the remainder of the arterial system. Frequently, the aorta must be dissected away from adjacent tissue to facilitate placement of such a cross-clamp.

To arrest cardiac function, a catheter is introduced through the sternotomy or thoracotomy and inserted through a puncture in the aortic wall into the ascending aorta between the cross-clamp and the aortic valve. Cardioplegic fluid is infused through the catheter into the aortic root and coronary arteries to perfuse the myocardium. An additional catheter may be introduced into the coronary sinus for retrograde perfusion of the myocardium with cardioplegic fluid. In addition, the myocardium is sometimes cooled by irrigation with cold saline solution and/or application of ice or cold packs to the outside of the heart. Cardiac contractions will then cease.

In surgical procedures requiring a median sternotomy or other form of gross thoracotomy, the ascending aorta is accessible for placement of an external cross-clamp through the large opening in the chest. However, such open-chest surgery often entails weeks of hospitalization and months of recuperation time as well as pain and trauma suffered by the patient. Moreover, the average mortality rate associated with this type of procedure is about two to fifteen per cent for first-time surgery, and mortality and morbidity are significantly increased for reoperation.

New devices and methods are therefore desired to facilitate the performance of cardiac procedures such as heart valve repair and replacement, coronary artery bypass grafting, and the like, using minimally invasive techniques, eliminating the need for a gross thoracotomy. Such techniques are described in U.S. Pat. No. 5,452,733, and application Ser. No. 08/163,241 filed Dec. 6, 1993, which are assigned to the assignee of the present invention and are incorporated herein by reference. In those applications, methods and devices are described for performing coronary artery bypass grafting, heart valve repair and replacement, and other procedures through small incisions or cannulae positioned in the chest wall, obviating the need for a gross thoracotomy. One technique described for arresting the heart during such procedures involves the use of a catheter which is introduced into a peripheral artery such as a femoral artery and positioned in the ascending aorta. An expandable member at the distal end of the catheter is expanded within the ascending aorta to block blood flow therethrough. Cardioplegic fluid is then be infused into the aortic root and into the coronary arteries through a lumen in the catheter, and/or in a retrograde manner through a catheter positioned in the coronary sinus, paralyzing the myocardium.

While this endovascular technique for arresting the heart provides significant advantages over conventional open-chest techniques, in some circumstances the use of an endovascular device for aortic partitioning may be undesirable. For example, in some cases the patient's femoral arteries and other vessels in which such a device could be introduced may not be suitable for such introduction, due to inadequate vessel diameter, vessel stenosis, vascular injury, or other conditions. In addition, where a number of endovascular cannulae are to be introduced to support cardiopulmonary bypass, retroperfusion of cardioplegic fluid, removal of blood from the heart, and other functions, a suitable arterial location for introduction of an endovascular aortic partitioning device may not be available. Further, it may be desirable to minimize the number of arterial punctures so as to reduce the risk of infection and other complications stemming from such punctures.

The present invention also provides an improved method and apparatus for clamping a patient's internal mammary artery for performing a coronary artery bypass procedure. In order to use a mammary arterial graft in a coronary artery bypass procedure, blood flow through the target mammary artery is temporarily stopped using a removable surgical clamp. In a conventional open-chest procedure, a relatively large, easy to handle clamp is applied by hand or with a forceps directly to the mammary artery through the large opening in the patient's chest provided by a median sternotomy. After the mammary artery is clamped, the mammary artery is ligated and divided at a location downstream from the clamp to create a free end which is connected to the coronary artery. After the grafting is complete, the clamp is removed by the surgeon, typically by hand or with the open forceps, to permit blood to flow through the mammary artery and into the coronary artery downstream of the blockage. As discussed above, gross thoracotomies used in conventional open heart surgery are highly traumatic to the patient and, therefore, new methods of performing surgery on the heart using minimally-invasive techniques have been recently developed. A further application of the present invention is for clamping the internal mammary artery for performing a coronary artery bypass procedure when performing minimally invasive heart surgery.

SUMMARY OF THE INVENTION

The present invention provides less-invasive devices and methods for clamping a body structure. An application of the present invention is described in connection with temporarily clamping a patient's internal mammary artery for performing a coronary artery bypass. Although the present invention is described in connection with clamping of the internal mammary artery, it is understood that the methods and apparatus described herein may be used to clamp any other body structure in a patient.

In a preferred embodiment of the invention, the clamp assembly includes a clamp, a handle, and a cable housed within a sheath extending between the clamp and the handle. The handle includes a cable puller and a first sheath holder. A proximal end of a cable is connected to the cable puller and a proximal end of the sheath is held by the first sheath holder. The clamp is coupled to the distal end of the cable and sheath. The clamp includes a first jaw which is movable between an open position and a closed position relative to a second jaw. In a preferred embodiment, the second jaw is also movable between the open and closed positions. The first and second jaws preferably move parallel to one another so that shear forces are not applied to the body structure thereby minimizing trauma to the body structure. Parallel jaws also offer a uniform force distribution over the length of the jaws. The first and second jaws may, of course, also move in any other manner relative to one another. The cable puller is preferably slidably mounted to the handle. The cable puller may also be coupled to the handle in any other manner. For example, the cable puller may be rotatably coupled to the handle.

An actuator is coupled to the cable puller for actuating the first jaw. A spring is mounted to the handle or clamp for providing a biasing force between the cable and the sheath. The spring preferably has a side which contacts the actuator for biasing the actuator. The actuator is preferably threadably coupled to the cable puller so that rotation of the actuator changes the compression of the spring thereby changing the clamping force exerted by the first and second jaws. The spring is preferably mounted so that the cable and cable puller extend through the spring.

The clamp assembly of the present invention provides a clamp which can be actuated from a location remote from the clamp and is therefore suitable for minimally invasive surgical techniques such as the coronary artery bypass procedure described above. An advantage of the clamp of the present invention is that the cable and sheath are flexible so that the clamp can be positioned in a convenient location which does not hinder access or use of other instruments. Another advantage of the present invention is that the flexible cable and sheath can be positioned through an instrument delivery member, such as a trocar, cannula, or retractor, while permitting other instruments to pass through the same instrument delivery member with minimal interference. In this manner, the number of openings in the patient is minimized.

The clamp assembly of the present invention also preferably includes an introducer which is releasably attached to the clamp. The introducer is more rigid than the cable and sheath so that the introducer may be used to position the clamp around the desired body structure. The introducer is preferably releasably coupled to the handle but may also be completely independent of the handle. The introducer is preferably malleable so that it can be deformed into a desired shape for positioning the clamp around other body structures in the patient if a curved path to the clamped body structure is required.

Because the patient's chest is preferably closed during the procedure except for one or more small percutaneous intercostal penetrations, visualization within the thoracic cavity is usually required to facilitate accurate positioning of the clamp and/or the delivery cannula. In an exemplary embodiment, a viewing device such as an endoscope or thoracoscope is positioned in a percutaneous intercostal penetration in the patient's chest to facilitate viewing at least a portion of the thoracic cavity. Other viewing devices may also be used which use ultrasound, transesophageal echocardiography, fluoroscopy, and the like. Although it is preferred to use an indirect visualization device, a small incision may be provided between adjacent ribs for direct visualization.

The terms "percutaneous intercostal penetration" and "intercostal penetration" as used herein refer to a penetration, in the form or a small cut, incision, hole, cannula, trocar sleeve, or the like through the chest wall between two adjacent ribs, wherein the patient's rib cage and sternum remain substantially intact, without cutting, removing, or significantly displacing the ribs or sternum. These terms are intended to distinguish between a gross thoracotomy, wherein the sternum and/or one or more ribs are cut or removed from the rib cage, or one or more ribs are retracted significantly, to create a large opening into the thoracic cavity. A "percutaneous intercostal penetration" may abut or overlap the adjacent ribs between which it is formed, but the maximum width of the penetration which is available for introduction of instruments into the thoracic cavity will be the width of the intercostal space, bounded by two adjacent ribs in their natural, substantially undeflected positions. It should be understood that one or more ribs may be retracted or deflected a small amount and/or a small amount of intercostal cartilage may be removed without departing from the scope of the invention, however, it is an objective of the invention to avoid the pain, trauma, and complications which result from large incisions and/or significant deflection or cutting of ribs in conventional, open-chest techniques.

A further understanding of the nature and advantages of the invention may be realized by reference to the remaining portions of the specification and drawings. It should be understood that while the invention is described in the context of thoracoscopic surgery on the mammary and coronary arteries, the system and method disclosed herein are equally useful on other types of body structures in the abdomen, pelvis, thorax and other body cavities.

BRIEF DESCRIPTION OF THE DRAWINGS

FIG. 1 is a perspective view of a first embodiment of a thoracoscopic aortic clamping device.

FIG. 2A is a side cross-sectional view of the aortic clamping device of FIG. 1.

FIG. 2B is a distal end view of the aortic clamping device of FIG. 1.

FIG. 3 is a perspective view of a second embodiment of a thoracoscopic aortic clamping device.

FIG. 4A is a side cross-sectional view of a proximal portion of the aortic clamping device of FIG. 3.

FIG. 4B is a side cross-sectional view of a distal portion of the aortic clamping device of FIG. 3.

FIG. 4C is a distal end view of the aortic clamping device of FIG. 3.

FIG. 5A is a side cross-sectional view of a further embodiment of a thoracoscopic aortic clamping device showing a proximal portion thereof.

FIG. 5B is a side cross-sectional view of a distal portion of the aortic clamping device of FIG. 5A.

FIG. 5C is a distal end view of the aortic clamping device of FIG. 5A.

FIG. 5D is a front view of a staple for closing an aortic puncture in the aortic clamping device of FIG. 5A.

FIG. 5E is a top view of the staple of FIG. 5D.

FIGS. 6A–6D are side cross-sectional views of a distal portion of the aortic clamping device of FIGS. 5A–5D showing the delivery cannula penetrating the aortic wall and a staple closing a puncture in the aortic wall.

FIG. 7 is a side partial cross-sectional view of a further embodiment of a thoracoscopic aortic clamping device and delivery cannula.

FIG. 8 is a side view of a distal portion of the aortic clamping device of FIG. 7.

FIG. 9 is a side cross-sectional view of the delivery cannula in the aortic clamping device of FIG. 7.

FIG. 10A is a side cross-sectional view of another embodiment of an aortic clamping device and delivery cannula.

FIG. 10B is a top view of a distal portion of the aortic clamping device of FIG. 10A in a unclamped position.

FIG. 11 is a top view of a distal portion of the aortic clamping device of FIG. 10A in a clamped position.

FIGS. 12A–12B are side views showing the aortic clamping device of FIG. 10A positioned in the patient's ascending aorta in an open position and a clamped position, respectively.

FIGS. 13 and 14 are side views illustrating alternative embodiments of the aortic clamping device of FIG. 10A positioned in the patient's ascending aorta.

FIG. 15 is a front view of a patient showing the positioning of the delivery cannula and cardiopulmonary bypass cannulae in the patient's circulatory system to facilitate arresting cardiac function.

FIG. 16 is a front view of the interior of a patient's thoracic cavity illustrating the positioning of the aortic clamping device of FIG. 3 about the patient's ascending aorta.

FIG. 25 is a side view of a further clamping assembly in which the jaws are actuated with a drive rod.

FIG. 26 is an end view of the clamp of FIG. 25 taken along line 26—26.

FIGS. 27A–B are enlarged cross-sectional views of the proximal portion of the clamp of FIG. 25 in the closed and opened positions.

FIG. 30A is a side view of a further clamping assembly showing the clamp in a closed position and the distal end of the clamp positioner adjacent the clamp.

FIG. 30B illustrates the clamp of FIG. 30A in an open position with portions broken away to show internal detail.

FIG. 30C is a plan view of the distal end of the clamp positioner of FIG. 30A.

FIG. 31A is a further clamping assembly in which the clamp positioner includes a coaxial cable to actuate the jaws of the clamp.

FIG. 31B shows an alternative embodiment of the clamp of FIG. 31A using a torsion spring.

FIG. 31C shows a further alternative embodiment of the clamp of FIG. 31A in which the jaws move along straight lines relative to one another and a compression spring is used to bias the jaws.

FIG. 37 shows the clamp assembly of FIG. 35 with the clamp having a high clamping force.

FIG. 38 shows the jaws of the clamp partially open.

FIG. 39 shows the jaws in the fully open position.

FIG. 40 is a side view of a first jaw.

FIG. 41 is a side view of a second jaw with a jaw member attached.

FIG. 42 is a plan view of the first and second jaws.

FIG. 43 is a side view of the jaw member.

FIG. 44 is an enlarged cross-section of the clamp of FIG. 39 along line A—A of FIG. 39.

FIG. 45 is a side view of a slide.

FIG. 46 is a plan view of the slide.

FIG. 47 is a side view of an anchor.

FIG. 48 is a plan view of the anchor.

FIG. 49 shows the malleable introducer mounted to the clamp and the handle.

FIG. 50 is a plan view of an alternative handle for the clamp assembly of FIGS. 35–49 with a spring force indicator.

FIG. 51 is a partial cross-sectional view of the handle of FIG. 50.

DESCRIPTION OF THE PREFERRED EMBODIMENTS

Figure 17:
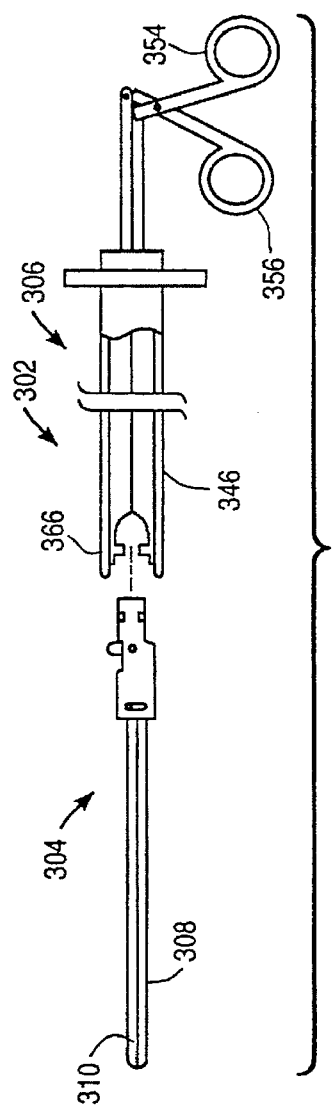
FIG. 17 is an external view showing a clamp assembly having a clamp and a clamp positioner.

A first preferred embodiment of a thoracoscopic aortic clamping device according to the invention is illustrated in FIGS. 1, 2A, and 2B. Device 20 includes a tubular outer shaft 22 having a proximal end 24 and a distal end 26. Outer shaft 22 preferably has a length of about 10 to 35 cm so that distal end 26 may reach the ascending aorta from a lateral side or an anterior side of the chest. A drive shaft 28 extends through outer shaft 22 and is axially rotatable therein. A fixed jaw 30 is mounted to distal end 26 of outer shaft 22. A movable jaw 32 is mounted to distal end 33 of drive shaft 28 in opposition to jaw 30 so as to facilitate clamping the aorta therebetween. Jaws 30, 32 each have a contact surface 34 configured to engage the exterior of the aorta, which may include textural features to enhance grip on the aorta. An elastomeric pad or cover (not shown) of silicone or other low durometer material may further be provided over contact surfaces 34 to reduce trauma on aortic tissue.

An actuator 36 is mounted at proximal end 24 of outer shaft 22. Actuator 36 includes a handle 38 mounted to proximal end 24 of outer shaft 22, and a movable handle 40 mounted to drive shaft 28. By pivoting handle 40 relative to handle 38, drive shaft 28 rotates within outer shaft 22, thereby opening and closing jaws 30, 32. A pair of notched extensions 42 on handles 38, 40 are configured to engage one another as the handles are closed, providing ratcheted locking of the device to maintain the jaws in a closed position.

Device 20 further includes a delivery cannula 44 for delivering cardioplegic fluid into the aorta while jaws 30, 32 are in a closed position on the aorta. Delivery cannula 44 has a proximal end 46 and a distal end 48 to which a needle 50 is attached. Needle 50 is dimensioned and configured to penetrate the ascending aortic wall into the aortic lumen, preferably having a length of about 1 cm to 3 cm. A delivery lumen 52 extends through cannula 44 and is in fluid communication with a port 54 near the distal end of needle 50. A luer fitting 56 is mounted to proximal end 46 of cannula 44, and is configured to engage a complementary luer fitting 58 mounted to the proximal end of drive shaft 28. Luer fitting 56 includes a barb 60 for connecting a hose (not shown) for delivering cardioplegic fluid into delivery lumen 52. Usually, the hose will be connected to a cardioplegic fluid pump designed to deliver a continual or periodic flow of cardioplegic fluid into the aorta during a procedure.

It may be seen that jaws 30, 32 are offset from the central longitudinal axis of outer shaft 22 and drive shaft 28 so as to permit introduction of needle 50 into the aorta upstream from the point at which jaws 30, 32 clamp the aorta.

Needle 50 is usually in the range of 10 gauge to 16 gauge so as to facilitate infusion of cardioplegic fluid into the aorta at a rate sufficient to paralyze the myocardium and to maintain such paralysis. Preferably, the size of needle 50 is minimized so that the puncture made in the ascending aorta will not bleed excessively when needle 50 is withdrawn from the aortic wall. However, in some cases, the puncture will require closure by means of sutures, staples, or other means, as described more fully below. To avoid the need for such closure, a plurality of smaller needles may be mounted to distal end 48 of delivery cannula 44 as an alternative to a single larger needle 50. The number and size of the needles are selected to provide an adequate total flow rate of cardioplegic fluid into the aorta, yet each needle is sufficiently small, e.g. less than about 0.025 in. outer diameter, so that each puncture need not be closed after withdrawal of the needles from the aortic wall due to normal blood clotting.

A second preferred embodiment of a thoracoscopic aortic clamping device according to the invention is illustrated in FIGS. 3 and 4A-4C. In this embodiment, device 64 includes a tubular outer shaft 66 having a proximal end 68 and a distal end 70. A tubular inner shaft 72 is slidably disposed within outer shaft 66 and has a proximal end 74 and a distal end 76. A pair of jaw extensions 78, 80 are disposed within inner shaft 72, each having an outwardly angled distal portion 79, 81 to which is attached one of offset jaws 82, 84. A core tube 86 is disposed between jaw extensions 78, 80 within inner shaft 72, and an inner lumen 88 extends through core tube 86. Delivery cannula 44 (described above) may be inserted through inner lumen 88 so that needle 50 extends distally from the distal end 76 of inner shaft 72. As best illustrated in FIG. 4C, jaws 82, 84 are offset from the central longitudinal axis of outer shaft 70 and inner shaft 76 so as to permit introduction of needle 50 into the aorta upstream from the point at which jaws 82, 84 clamp the aorta. Jaws 82, 84 may have a pair of elastomeric pads 83, 85 of silicone or other low durometer material to reduce trauma when clamped on the aorta.

A handle 90 is attached to the proximal end 68 of outer shaft 66 and includes a housing 92 to which is coupled a lever 94. A pin 96 extends through a distal end 98 of lever 94, and is slidable within a pair of slots 100 in housing 92. A link 102 is pivotally coupled at one end to lever 94 in a middle portion thereof, and at the other end to housing 92 proximal to slots 100. Inner shaft 72 is attached at its proximal end 74 to distal end 98 of lever 94. In this way, pivoting lever 94 toward housing 92 translates the lever distally within slots 100, thus translating inner shaft 72 distally over jaw extensions 78, 80. Distal end 76 of inner shaft 72 engages angled distal portions 79, 81 of jaw extensions 78, 80, thus urging jaws 82, 84 toward each other. A spring (not shown) may be mounted between housing 92 and lever 94 to bias lever 94 against housing 92 to maintain jaws 82, 84 in a closed or clamped position.

Core tube 86 is fixed to housing 92 at a proximal end 104 thereof. A luer fitting 106 is mounted to the exterior of housing 92 and has an interior passage in communication with inner lumen 88. When jaws 82, 84 have been clamped onto the patient's aorta, delivery cannula 44 may be inserted through inner lumen 88 until needle 50 penetrates the aortic wall upstream of jaws 82, 84. Luer fitting 56 on delivery cannula 44 may be locked onto luer fitting 106 on housing 92. A hose may be connected to barb 60 on delivery cannula 44 to deliver cardioplegic fluid into the aorta through delivery lumen 52.

As described above, the aortic puncture created by needle 50 may sometimes require closure after withdrawal of the needle to prevent excessive bleeding when cardiac function is restored. Such closure may be performed by means of thoracoscopic instruments, such as staple appliers or suturing instruments. Alternatively, a means for closing the aortic puncture may be integrated into the aortic clamping device of the invention. An example of such a device is illustrated in FIGS. 5A–5D and 6A–6D. In this embodiment, clamping device 110 comprises the same jaw configuration, handle, and jaw closure mechanism as the embodiment of FIGS. 3 and 4A–4B. Device 110 further includes an inner sleeve 112 slidably disposed within core tube 86 and having a proximal end 114, a distal end 116 and a lumen 118 therebetween. A delivery tube 120 resides within lumen 118 and has a fitting 122 at its distal end to which a needle 124 is attached.

Distal end 116 of inner sleeve 112 is configured to retain a staple 126 within lumen 118. Staple 126 comprises, as shown in FIGS. 5D–5E, at least two legs 128, 130 connected by a flexible cross member 132. Legs 128, 130 have distal points 134, 136 for penetrating aortic wall tissue. In an unstressed condition, legs 128, 130 are disposed at an angle between about 60° and 87° relative to cross member 132 such that points 134, 136 are closer together than the remainder of legs 128, 130. Legs 128, 130 may be deflected outward so as to be parallel to each other, whereby cross member 132 is deflected into a curved configuration, (shown in phantom in FIG. 5D). When legs 128, 130 are released, cross-member 132 resiliently returns to its unstressed shape, returning legs 128, 130 to their angled disposition. In this way, staple 126 may be applied to the aorta with legs 128, 130 parallel, and, when released, legs 128, 130 crimp the aortic tissue therebetween without requiring a separate crimping or closure means. In alternative configurations, staple 126 may have three, four, or more legs with inwardly disposed distal points. Shallow axial channels (not shown) may be provided on opposing sides of lumen 118 extending proximally from distal end 116 in which legs 128, 130 may be retained to maintain axial alignment of staple 126.

As shown in FIG. 5E, cross member 132 has a bore 138 in a middle portion thereof that is larger than needle 124, but smaller than fitting 122. The staple is held within lumen 118 so that needle 124 is aligned with bore 138. As shown in FIGS. 6A–6B, by distally advancing sleeve 112 and delivery tube 120 in tandem, needle 124 penetrates the aortic wall while staple 126 is applied to aorta A with legs 128, 130 parallel. Sleeve 112 may then be retracted proximally while delivery tube 120 remains in position, wherein fitting 122 holds staple 126 in the aortic wall and legs 128, 130 return to their unstressed, angled configuration (FIG. 6C). When cardioplegic fluid delivery is complete, delivery tube 120 may be retracted, removing needle 124 from aorta A and leaving staple 126 in the aortic wall to close the puncture created by needle 124 (FIG. 6D).

The means for actuating sleeve 112 and delivery tube 120 will be described with reference to FIG. 5A. An actuation button 140 is mounted at the proximal end of housing 92 and is biased in an outward position by a spring 142. Actuation button 140 is coupled to an adaptor 144 fixed to proximal end 146 of delivery tube 120. Adaptor 144 has an inner chamber (not shown) in communication with the interior of delivery tube 120. An arm 148 on adaptor 144 has an inner passage (not shown), in communication with the inner chamber of adaptor 144 and is configured for connection to a flexible tube 150. Tube 150 connects to a fitting 152 mounted to housing 92, which may be connected to a hose 154 from a cardioplegic fluid delivery device.

A pawl 156 is pivotally mounted to adaptor 144 and is biased by a spring (not shown) to engage a set of linear teeth 158 on housing 92, thus providing a ratcheted locking mechanism to maintain actuator button 140 in a depressed position. A catch 160 is pivotally mounted to adaptor 144 and is biased in a counter-clockwise direction. As actuator button 140 is depressed, delivery tube 120 advances distally relative to sleeve 112 until catch 160 engages proximal end 114 of sleeve 112, at which point needle 124 and staple 126 are in the position shown in FIG. 6A. Further depression of actuator button 140 advances delivery tube 120 and sleeve 112 in tandem, allowing needle 124 and staple 126 to penetrate the aortic wall, as shown in FIG. 6B. Delivery of cardioplegic fluid into aorta A may then be initiated through hose 154, tube 150, delivery tube 120, and needle 124. When the procedure is complete, cardioplegic fluid delivery is terminated and a release button 162 is pressed, which pivots catch 160 in a clockwise direction, allowing sleeve 112 to retract proximally under the force of a spring 164 disposed about the proximal end of sleeve 112. At this point, sleeve 112, delivery tube 120, and staple 126 are in the positions shown in FIG. 6C. Sleeve 112 retracts relative to delivery tube 120 until its proximal end 114 engages a release arm 166 on pawl 156, disengaging pawl 156 from teeth 158 and allowing delivery cannula 120 and actuator button 140 to retract. In this way, with the press of a single release button, needle 124 is removed from aorta A and staple 126 is applied to aortic wall to close the puncture created by needle 124, as illustrated in FIG. 6D. Staple 126 may remain in the patient's body indefinitely, may be resorbable, or may be surgically removed using thoracoscopic instruments after clotting has occurred or the aortic puncture has healed.

A further embodiment of an aortic clamping device according to the invention is illustrated in FIGS. 7–9. In this embodiment, clamping device 170 is constructed in large part like the embodiment of FIGS. 3 and 4A–4C, except that no inner lumen 88 is required for insertion of a delivery cannula 44, and that jaws 82, 84 need not be offset from the central axis of shafts 66, 72 to allow the delivery cannula to penetrate the aorta upstream from the point at which the aorta is clamped. In the present embodiment, the need to penetrate the aorta is obviated by the use of an endovascular delivery cannula 172 positioned within the aortic lumen between jaws 82, 84. As shown in FIG. 9, delivery cannula 172 comprises a flexible shaft 174 of a biocompatible polymer such as polyurethane, polyvinyl chloride, polyether block amide, or polyethylene, with a distal end 176, a proximal end 178, and at least one inner lumen 180 therebetween. A port 182 is disposed at distal end 176 in fluid communication with inner lumen 180, to facilitate infusion of cardioplegic fluid into the aorta. A soft tip 184 may be provided on distal end 176 to reduce the risk of injury to vessel walls, to the aortic valve, or to other tissue. A second lumen 186 may also be provided with a port 188 near distal end 176, to facilitate infusion or aspiration of fluids, pressure measurement, and the like. An adaptor 190 is attached to proximal end 178 and has a first arm 192 with a passage 193 in communication with inner lumen 180 and a second arm 194 with a passage 195 in communication with second lumen 186. First arm 192 may be connected to a hose from a cardioplegic fluid delivery pump, while second arm 194 may be connected to a pressure measurement device, aspiration device, fluid delivery device, or the like.

As illustrated in FIGS. 7–8, delivery cannula 172 is positioned in the aorta A, with distal end 176 in the ascending aorta between the brachiocephalic artery and the coronary ostia. Shaft 174 preferably has a length of at least about 80 cm to allow introduction into a femoral artery and transluminal positioning of distal end 176 in the ascending aorta. First arm 192 may be connected to a cardioplegic fluid supply 196, while second arm 194 may be connected to a pressure measurement device 198. Jaws 82, 84 of aortic clamping device 170 are positioned about the ascending aorta A between the brachiocephalic artery and the coronary arteries. Jaws 82, 84 are then closed on aorta A by actuating lever 94, which extends inner shaft 66 over angled segments 79, 81. Jaws 82, 84 are closed until the opposing sides of aorta A engage one another and seal about the exterior of delivery cannula 172, as shown in FIG. 8. Cardioplegic fluid may then be delivered through inner lumen 180, while the pressure within the aorta upstream of clamping device 170 may be measured through second lumen 186.

Referring now to FIGS. 10A–10B and 11, a further embodiment of an aortic clamping device according to the invention will be described. In this embodiment, aortic clamping device 200 comprises a shaft 202 having a distal end 204, a proximal end 206, and first and second lumens 208, 210 extending therebetween. A flexible cable or strap 212 is slidably disposed in first lumen 208 and extends distally through an opening 214 in distal end 204. An anchor 216 is attached to the distal end of cable 212. A wire 218 is slidably disposed in second lumen 210 and has a loop 220 extending distally from distal end 204 of shaft 202. Loop 220 has a width which narrows in the distal direction, so that anchor 216 may be passed through a proximal portion of loop 220, and trapped in a distal portion of loop 220.

A handle 222 is attached to proximal end 204 of shaft 202 and has a grip 224 suitable for grasping with the user's hand. A lever 226 is pivotally mounted to handle 222 and has an upper end 227 to which a spring 228 is attached to bias upper end 227 in a proximal direction. Wire 218 has a second loop 230 at its proximal end to which is attached a flexible cord 232. Cord 232 extends around a pulley 234 rotatably coupled to handle 222 and attaches to upper end 227 of lever 226. A gear 233 is mounted to lever 226 and is engaged by a pawl 235 pivotally mounted to handle 222. Cable 212 extends through handle 222 and exits through an opening 236, with a proximal end 238 disposed outside of handle 222. An anchor ball 240 is attached to proximal end 238 and has a width larger than that of opening 236 to prevent passage therethrough. Anchor ball 240 may be configured to allow adjustment of its longitudinal position on cable 212 to facilitate use of device 200 on aortas of various sizes.

Usually, aortic clamping device 200 is used in conjunction with delivery cannula 172, described above in connection with FIGS. 7–9. As shown in FIGS. 12A–12B, delivery cannula 172 is first introduced into the patient's arterial system, usually through a femoral artery, and advanced so that distal end 176 is in the ascending aorta A between brachiocephalic artery B and coronary ostia C. Aortic clamping device 200 is positioned so that distal end 204 is adjacent the aorta at the point it is to be clamped. As shown in FIGS. 10A–10B, cable 212 is wrapped around aorta A, usually by means of conventional thoracoscopic instruments such as forceps and/or needle drivers, and anchor 216 is inserted through loop 220. Lever 226 is then actuated, drawing anchor 216 and cable 212 proximally through lumen 210 so as to tighten cable 212 around aorta A until the aortic wall seals against the exterior of delivery cannula 172, as shown in FIGS. 11 and 12B.

In an exemplary embodiment, as shown in FIGS. 12A–12B, delivery cannula 172 has a pad 242 of silicone or other low durometer polymer fixed to its exterior near distal end 176 to minimize trauma to the aortic wall and to resist movement of the cannula during clamping. A stiffener coil 244 embedded in shaft 174 may also be provided to maintain the patency of lumens 180, 186 during clamping. In addition, shaft 202 may be bendable to facilitate positioning shaft 202 through an intercostal space with distal end 204 near the ascending aorta.

To release aortic clamping device 200 from aorta A, cable 212 may be severed by inserting a scissors or knife through side port 246 in handle 222, thereby releasing tension on cable 212 and allowing the device 200 to be withdrawn from the thoracic cavity. Alternatively, anchor ball 240 may be configured to be removable from proximal end 238 of cable 212. Or, a release cord 248 coupled to pawl 235 may be provided to facilitate disengaging pawl 235 from gear 233, allowing lever 226 to return to its outward position, thereby releasing tension on cable 212. Anchor 216 may then be removed from loop 220 using thoracoscopic instruments, allowing device 200 to be removed from the thoracic cavity.

FIGS. 13 and 14 illustrate two alternative constructions of delivery cannula 172 in conjunction with aortic clamping device 200. In the embodiment of FIG. 13, delivery cannula 172 includes a balloon 250 attached to shaft 174 and spaced proximally from distal end 176 a sufficient distance to allow aorta A to be clamped about shaft 174 distal to balloon 250. The interior of balloon 250 is in communication with an inflation lumen (not shown) in shaft 174 for delivery of an inflation fluid into the balloon, and is configured to fully occlude the aortic lumen when inflated. A plurality of ports 252 are provided in shaft 174 distal to balloon 250 and are in communication with an aspiration lumen (not shown) within shaft 274. In this way, when cable 212 is released after a procedure, any air, fluids, thrombus, and/or other emboli which might have been produced are prevented from flowing downstream by balloon 250, and may be aspirated from the arterial system through ports 252.

In the embodiment of FIG. 14, delivery cannula 172 includes an aortic occlusion means 254 at distal end 176 of shaft 174. Occlusion means 254 is configured to completely occlude the aortic lumen, and may be funnel-shaped with a tapered interior passage in communication with an aspiration lumen (not shown) in shaft 174. In this way, air, fluids, thrombus, and/or other emboli which might be produced during a procedure distal to the point of clamping are trapped in occlusion means 254 and may be withdrawn from the arterial system through the aspiration lumen in delivery catheter 174. Occlusion means 254 is preferably a soft collapsible material to allow it to be collapsed and inserted into a sheath for introduction. The sheath may be positioned in the ascending aorta, then retracted to allow occlusion means 254 to expand and occlude aorta A. Aortic clamping device 200 may then be used to clamp aorta A about shaft 174.

The method of the invention will now be described with reference to FIGS. 15 and 16. The patient is first placed on cardiopulmonary bypass, using the system illustrated in FIG. 15. A venous cannula 260 is positioned in a vein V of the patient, preferably a femoral vein in the groin area, and advanced into the inferior vena cava IVC and/or into the interior of heart H to withdraw deoxygenated blood therefrom. Venous cannula 260 may alternatively be introduced thoracoscopically into the inferior vena cava IVC, into the superior vena cava SVC, or into the right atrium RA. Venous cannula 260 is connected to a cardiopulmonary bypass system 262 which receives the withdrawn blood, oxygenates the blood, and returns the oxygenated blood to an arterial return cannula 264 positioned in an artery AR, preferably a femoral artery. Arterial return cannula 264 may alternatively be introduced thoracoscopically directly into an ascending or descending portion of the aorta A.

A pulmonary venting catheter 266 may also be utilized to withdraw blood from the pulmonary trunk PT. Pulmonary venting catheter 266 may be introduced from the neck through the internal jugular vein JV and superior vena cava SVC, or from the groin through femoral vein V and inferior vena cava IVC. Usually, a Swan-Ganz catheter (not shown) is first introduced and positioned in pulmonary trunk PT using well-known techniques, and pulmonary venting catheter 266 is then introduced over the Swan-Ganz catheter. Blood is withdrawn from pulmonary trunk PT through a port at the distal end of pulmonary venting catheter 266 and an inner lumen extending through the catheter outside of the patient's body. Pulmonary venting catheter 266 may further have one or more balloons 268 at its distal end proximal to the distal port for occluding pulmonary trunk PT.

An alternative method of venting blood from pulmonary trunk PT is described in U.S. Pat. No. 4,889,137, which is incorporated herein by reference. In the technique described therein, a catheter is positioned from the internal jugular vein JV in the neck through the right atrium, right ventricle, and pulmonary valve into the pulmonary trunk PT. The catheter has a coil about its periphery which holds the pulmonary valve open so as to drain blood from pulmonary trunk PT, thereby decompressing the left side of the heart.

For purposes of arresting cardiac function, a delivery cannula 172 may be positioned in a femoral artery AR by a percutaneous technique such as the Seldinger technique, or through a surgical cut-down CD. Delivery cannula 172 is advanced, usually over a guidewire (not shown), until its distal end 176 is disposed in the ascending aorta AA between the coronary ostia C and the brachiocephalic artery B. Blood may be vented from ascending aorta AA through a port 182 at the distal end of delivery cannula 172 in communication with inner lumen 180 in delivery cannula 172, through which blood may flow to proximal end 178. The blood may then be directed to a blood filter/recovery system 270 to remove emboli, and then returned to the patient's arterial system via CPB system 262.

Ascending aorta AA may then be clamped using one of the various embodiments of aortic clamping device described above. FIG. 16 illustrates the use of aortic clamping device 110 of FIGS. 5A-5D. Shaft 66 of clamping device 110 is positioned through the chest wall and into the thoracic cavity TC through an intercostal space I between two adjacent ribs R. Another preferred entry for the shaft 66 is through a penetration on the patient's right hand side between the first and second ribs. A trocar sleeve may be positioned in the chest wall within an intercostal space to facilitate introduction of clamping device 110. An endoscope positioned in thoracic cavity TC through and intercostal space I may be used for visualization to facilitate accurate positioning of clamping device 110. Jaws 82, 84 are positioned on opposing sides of ascending aorta AA between brachiocephalic artery B and coronary ostia C (FIG. 15). Lever 94 is then actuated to close jaws 82, 84 on ascending aorta AA, stopping blood flow therethrough.

When it is desired to arrest cardiac function, a cardioplegic fluid such as potassium chloride (KC1) is delivered to the myocardium in at least one of several ways. Clamping device 110 includes an integrated cardioplegic fluid delivery cannula 120 (FIGS. 5A-5D), which may be activated by depressing actuator button 140 on handle 90. Needle 124 will penetrate the aortic wall upstream of jaws 82, 84, and cardioplegic fluid may be delivered into the ascending aorta by means of a cardioplegic fluid pump 276 connected to fitting 152 in communication with delivery cannula 120.

As alternative or addition to delivery by means of clamping device 110, cardioplegic fluid may be delivered in an anterograde manner from a cardioplegic fluid pump 196 through inner lumen 180 in delivery cannula 172 into the ascending aorta upstream of the point at which the aorta is clamped. The cardioplegic fluid flows from the ascending aorta AA into the coronary arteries and paralyzes the myocardium. It should be noted that, when using clamping device 110 with integrated delivery cannula 120, endovascular delivery cannula 172 need not be utilized. However, it may be desirable to utilize such a cannula to facilitate pressure measurement, aspiration of air, fluids, thrombus, and other emboli from the aortic lumen, as well as supplementary delivery of cardioplegic fluid.

In addition, cardioplegic fluid may be delivered in a retrograde manner through a retroperfusion catheter 272 positioned in the coronary sinus CS. Retroperfusion catheter 272 may be positioned, usually over a guidewire (not shown), from the neck through the internal jugular vein JV and superior vena cava SVC, or from the groin through a femoral vein V and the inferior vena cava IVC. Retroperfusion catheter 272 may have one or more balloons (not shown) at its distal end to enhance positioning and infusion of cardioplegia into the coronary sinus. Cardioplegic fluid may thus be infused through the coronary veins into the capillary beds, paralyzing the myocardium.

Following delivery of cardioplegic fluid into the aortic lumen, cardiac function will quickly cease. The patient is now prepared for an interventional procedure to be performed. A variety of thoracoscopic, endovascular, or open surgical procedures may be performed, including coronary artery bypass grafting, heart valve repair and replacement, septal defect repair, pulmonary thrombectomy, removal of atrial myxoma, patent foramen ovale closure, treatment of aneurysms, myocardial drilling, electrophysiological mapping and ablation, angioplasty, atherectomy, correction of congenital defects, and other interventional procedures. Less-invasive techniques for performing such procedures are described in commonly-assigned copending application Ser. No. 08/023,778, and application Ser. No. 08/163,241, both of which are incorporated herein by reference.

When it is desired to restore cardiac function, infusion of cardioplegic fluid through thoracoscopic delivery cannula 120, endovascular delivery cannula 172 and/or retroperfusion catheter 272 is discontinued. Blood, other fluids, air, thrombus, and other emboli within the heart or coronary arteries may then be aspirated through inner lumen 180 of delivery cannula 172, as well as through venous cannula 260 and/or pulmonary venting catheter 266. Release button 162 on clamping device 110 may then be depressed, causing needle 124 to retract from aorta A and leaving a staple 126 (FIGS. 6A–6D) in the aortic wall to close the puncture created therein. If the clamping device utilized does not include a means for closing the aortic puncture, conventional thoracoscopic instruments may be used to suture or staple the aortic puncture closed, if necessary.

Lever 94 on clamping device 110 may then be released, opening jaws 82, 84 to allow warm, oxygenated blood to flow into the coronary arteries to perfuse the myocardium. Cardiac contractions will usually begin soon thereafter. In some cases, electrical defibrillation may be necessary to help restore cardiac function. Clamping device 110 is withdrawn from the thoracic cavity. Any trocar sleeves used in the procedure are then removed, and thoracoscopic incisions are sutured or stapled closed. Delivery catheter 172 and retroperfusion catheter 272 may be removed from the patient. Cardiopulmonary bypass is then discontinued, and arterial cannula 264, venous cannula 260, and pulmonary venting catheter 266 are removed from the patient. Vascular punctures are closed.

The clamps described above are suitable for clamping hollow body structures in a patient, and in particular the ascending aorta, while the proximal end of the clamp extends through a percutaneous intercostal penetration in the patient. The following preferred embodiments describe deployable clamps which have clamp positioners which are detachable from the clamps. In this manner, the clamp positioner can be removed so that increased visual access is provided and, furthermore, a trocar used to introduce the clamp is available for another instrument thereby advantageously minimizing the number of penetrations in the patient.

Figure 18:
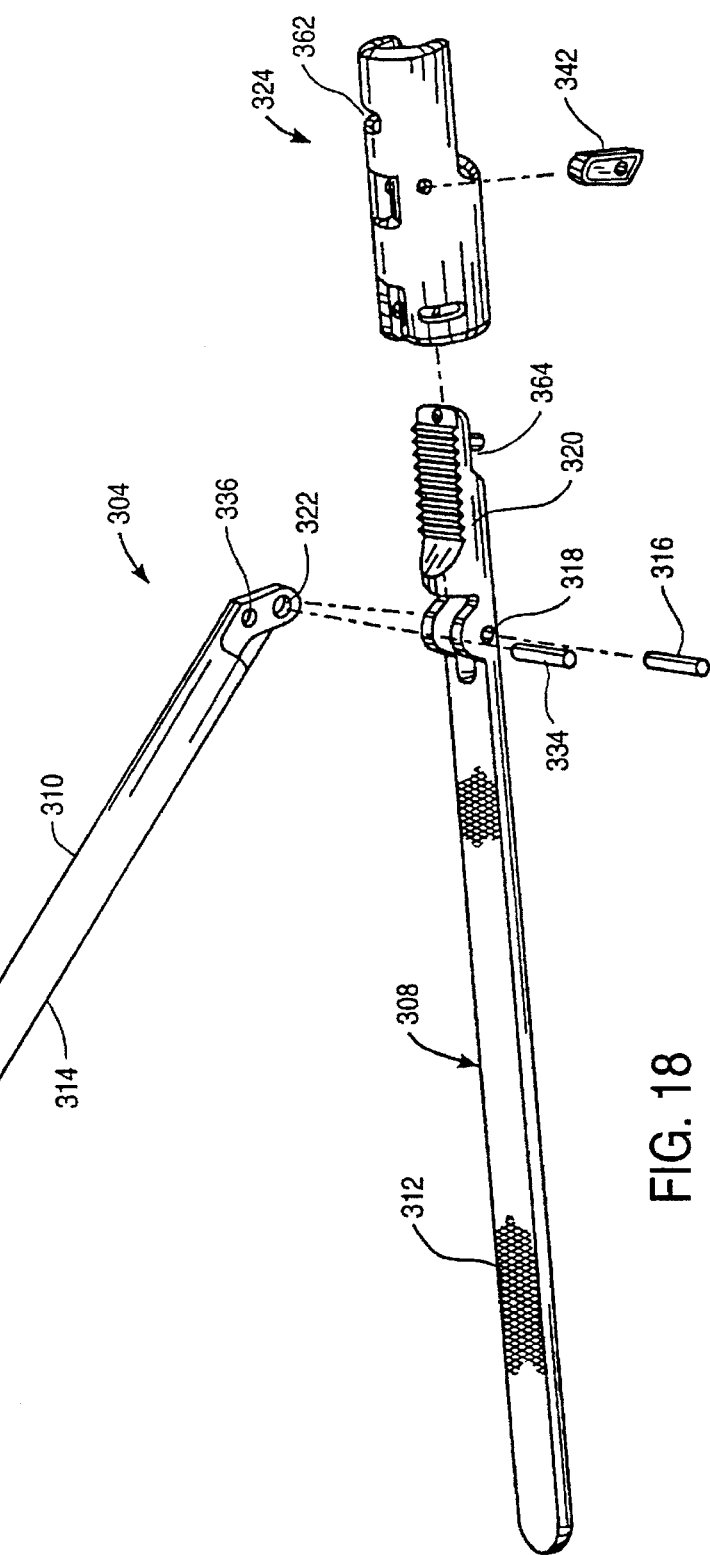
FIG. 18 is an exploded isometric view of the clamp of FIG. 17.

FIGS. 17 and 18 illustrates a clamp assembly 302 having a clamp 304 releasably connected to a clamp 306 positioner. The clamp 304 includes first and second jaws 308, 310 having opposed atraumatic jaw surfaces 312, 314. The jaw surfaces 312, 314 are generally flat although any jaw surface shape may be provided. The jaws 308, 310 are generally straight but may be provided with any other shape such as curved. Jaw 310 is pivotally mounted to jaw 308 by a pivot pin 316 which passes through a bore 318 formed in a jaw extension 320 of jaw 308. Pin 316 passes through a bore 322 formed at the proximal end of jaw 310.

Figure 19:
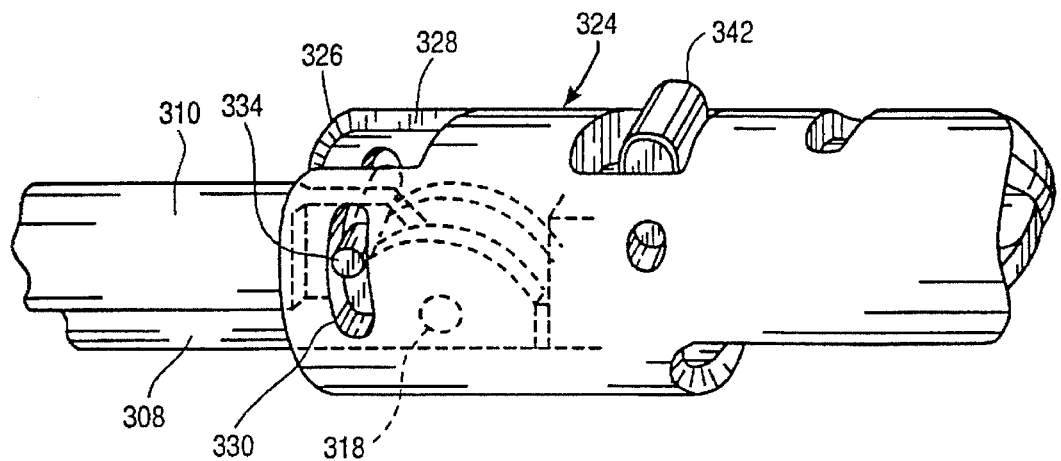
FIG. 19 is an enlarged external view of the proximal end of the clamp of FIG. 17.
Figure 20:
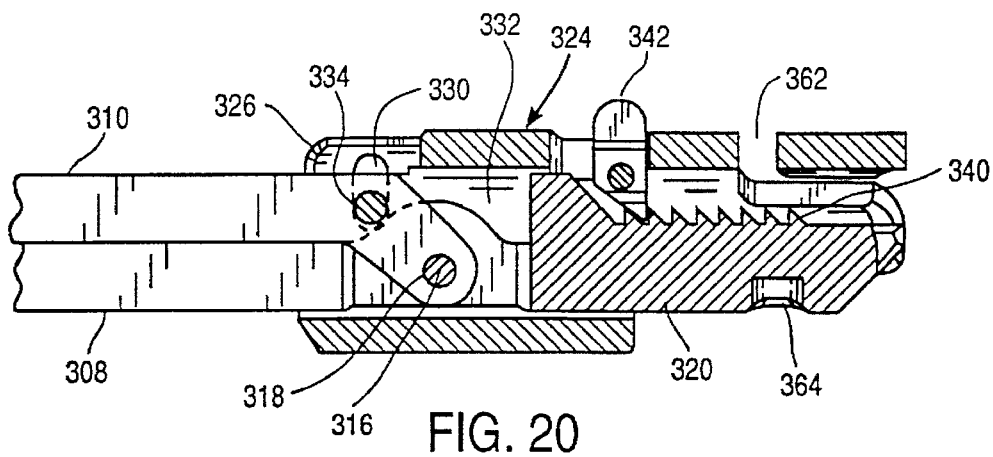
FIG. 20 is an enlarged cross-sectional view of the clamp of FIG. 19 with the jaws in a closed position.
Figure 21:
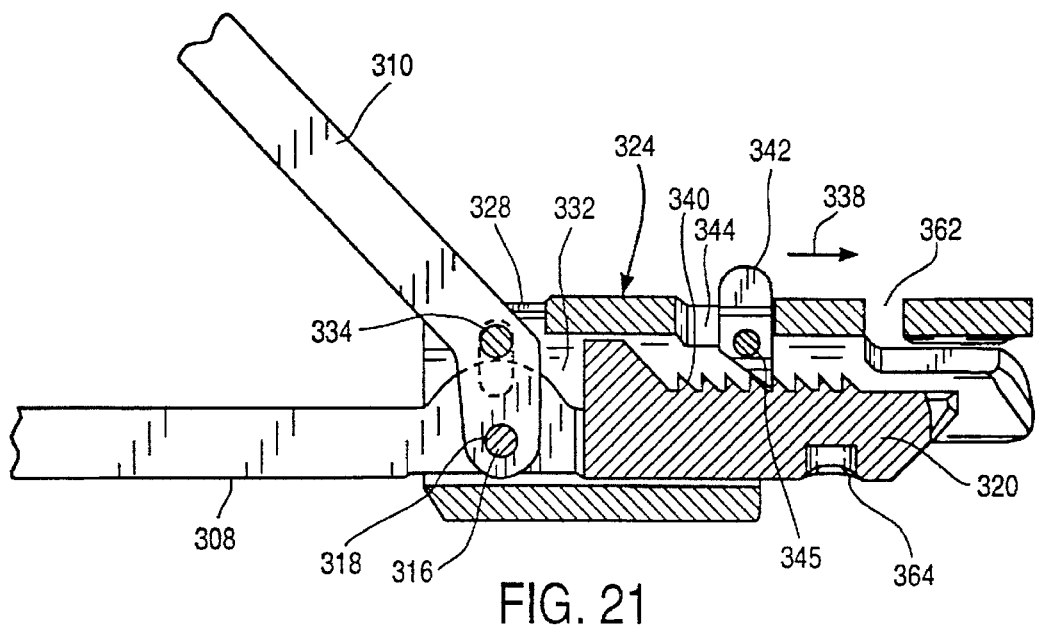
FIG. 21 is an enlarged cross-sectional view of the clamp of FIG. 19 with the jaws in an open position.

Referring to FIGS. 19–21, clamp 304 also includes an actuator housing 324 slidably mounted to jaw extension 320. The slidable actuator housing 324 moves the jaw 310 between open and closed positions through a pin and slot configuration, however, any other mechanical connection may be provided. A second pin 334 is fixed within a second bore 336 formed of the second jaw 310 in an interference fit. The ends of pin 334 reside within slots 330 so that movement of actuator housing 324 in the direction of arrow 338 of FIG. 21 causes pin 334 to move upwardly within slots 330 thereby pivoting jaw 310 upwardly from the closed position of FIG. 20 to the open position of FIG. 21. The distal end 326 of actuator housing 324 circumscribes jaw extension 320 and another slot 330 formed therein. Slot 328 passes into the open interior 332 of actuator housing 324 to permit the jaw 310 to pass therethrough when in the open position of FIG. 21.

Jaw extension 320 includes a set of ratchet teeth 340 for locking the jaws in the closed position. The ratchet teeth 340 are engaged by a pawl 342 pivotally mounted within a slot 344 at a pivot 345. Pawl 342 is biased by a spring, not shown, to pivot in a clockwise direction. Pawl is pivoted in a counterclockwise direction using the clamp positioner 306 to disengage pawl 342 from ratchet teeth 340.

Figure 22:
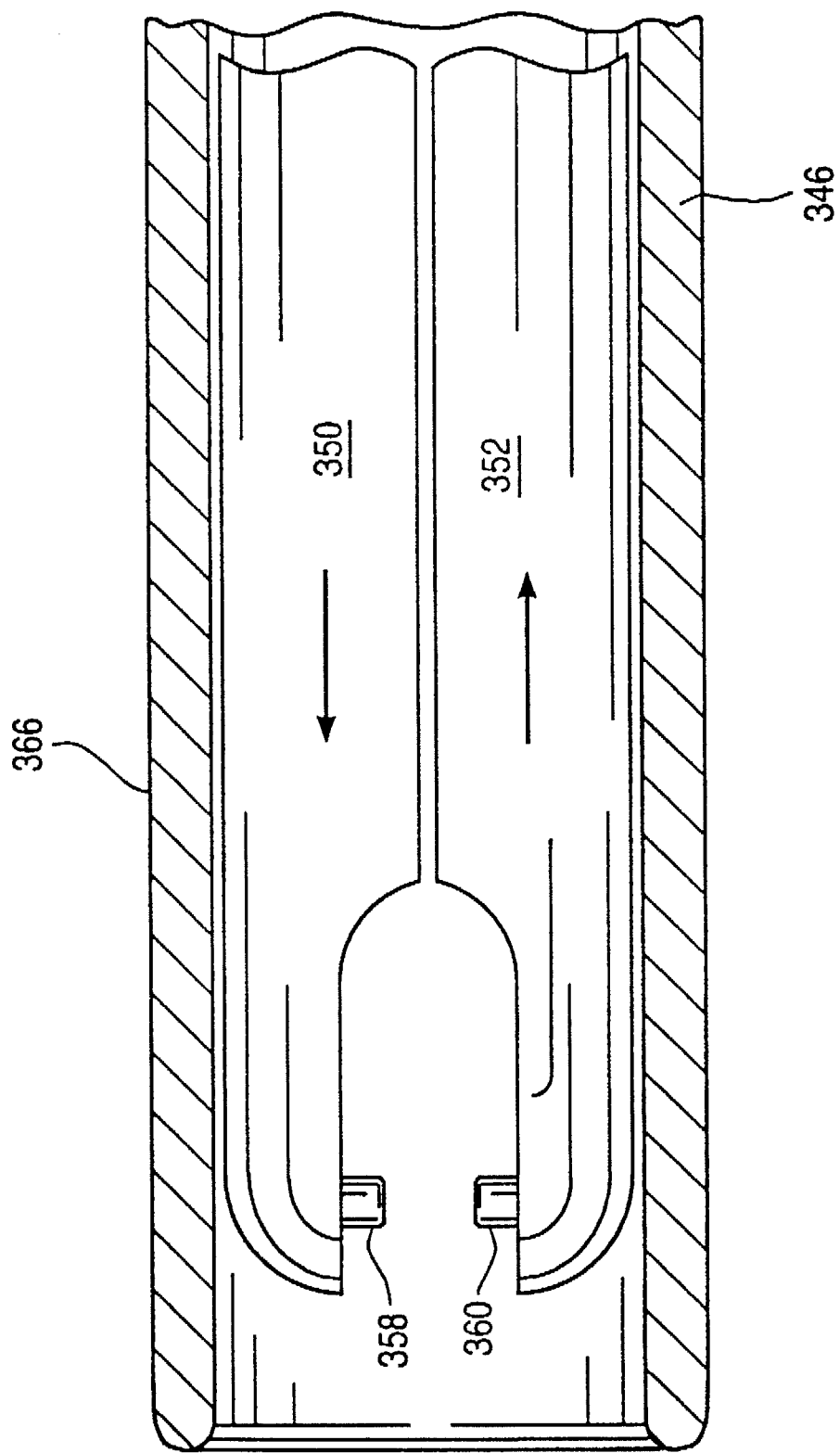
FIG. 22 is an enlarged view of the distal end of the clamp positioner of FIG. 17.

Referring now primarily to FIGS. 17 and 22, clamp positioner 306 includes an elongate hollow body 346 sized to fit within a trocar sleeve 348 (see FIG. 23) with clamp 304 mounted to the distal end of clamp positioner 306. Hollow body 346 houses a pair of longitudinally slidable manipulator rods 350, 352 coupled to hand grips 354, 356, respectively. Manipulator rods 350, 352 each has a lug 358, 360 which engages L-shaped slots 362, 364 formed in actuator housing 324 and jaw extension 320, respectively. Lugs 358, 360 and slots 362, 364 are sized so that the distal end 366 of hollow body 346 pivots pawl 342 in a counter-clockwise direction when the lugs 358, 360 are positioned in the slots 362, 364. This unlocks jaw 310 and permits moving the jaws 308, 310 to the open position of FIG. 21 with handles 354, 356. The clamp 304 is locked again by rotating and pulling clamp positioner 306 so that the lugs 358, 360 disengage from slots 362, 364 thereby releasing pawl 342 and permitting pawl 342 to return to the position of FIG. 20. The clamp positioner 306 is then preferably withdrawn from thoracic cavity TC through trocar sleeve 348 leaving clamp 304 in the patient.

Figure 23:
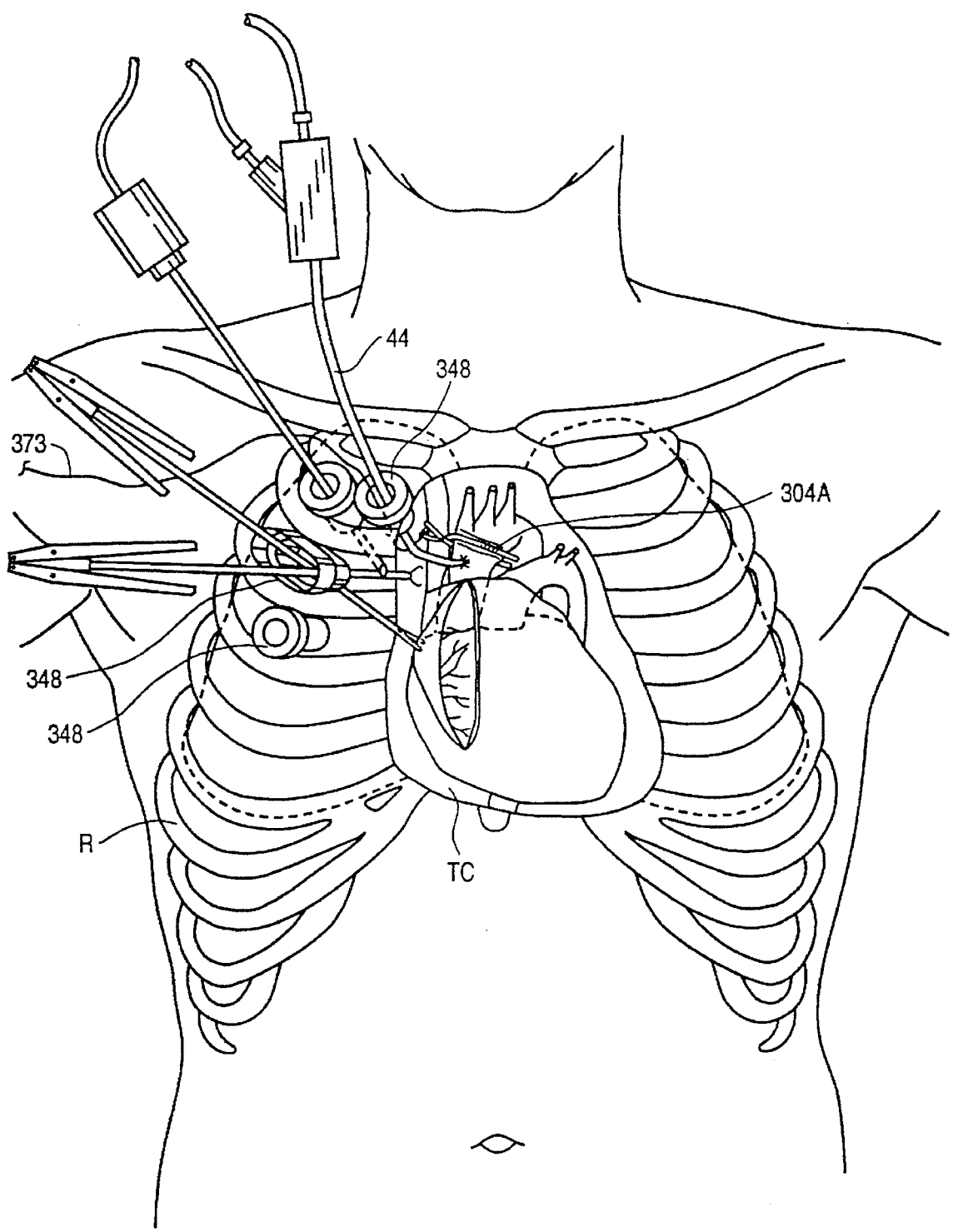
FIG. 23 is a front view of the interior of a patient's thoracic cavity illustrating the use of trocar sleeves between the patient's ribs to introduce various thoracoscopic surgical devices into the thoracic cavity and a detachable clamp clamping the ascending aorta during a surgical procedure.
Figure 24:
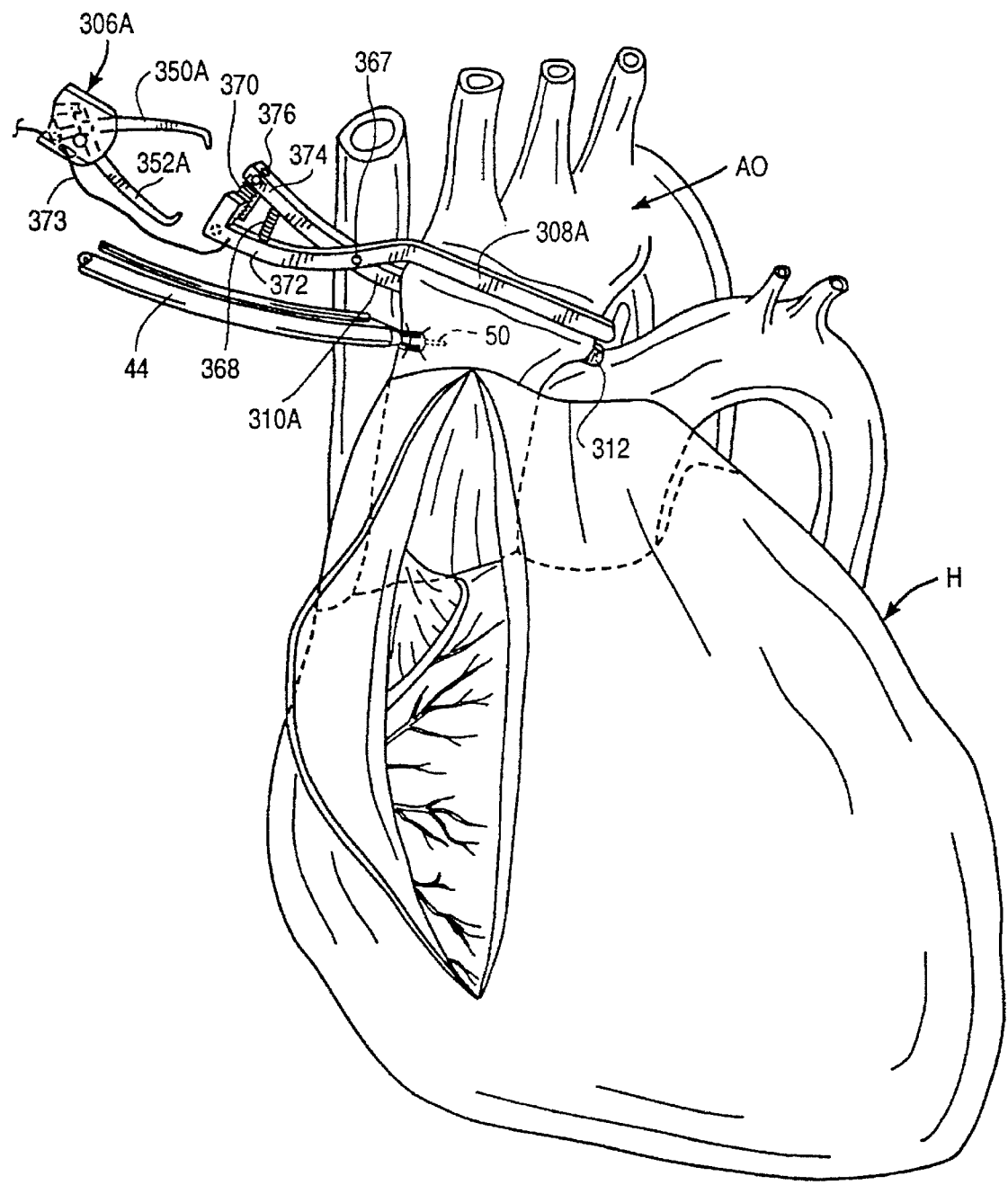
FIG. 24 is an enlarged view of a portion of FIG. 23 illustrating the distal end of an alternative clamp positioner used with the alternative clamp of FIGS. 23 and 24.
Figure 27A:
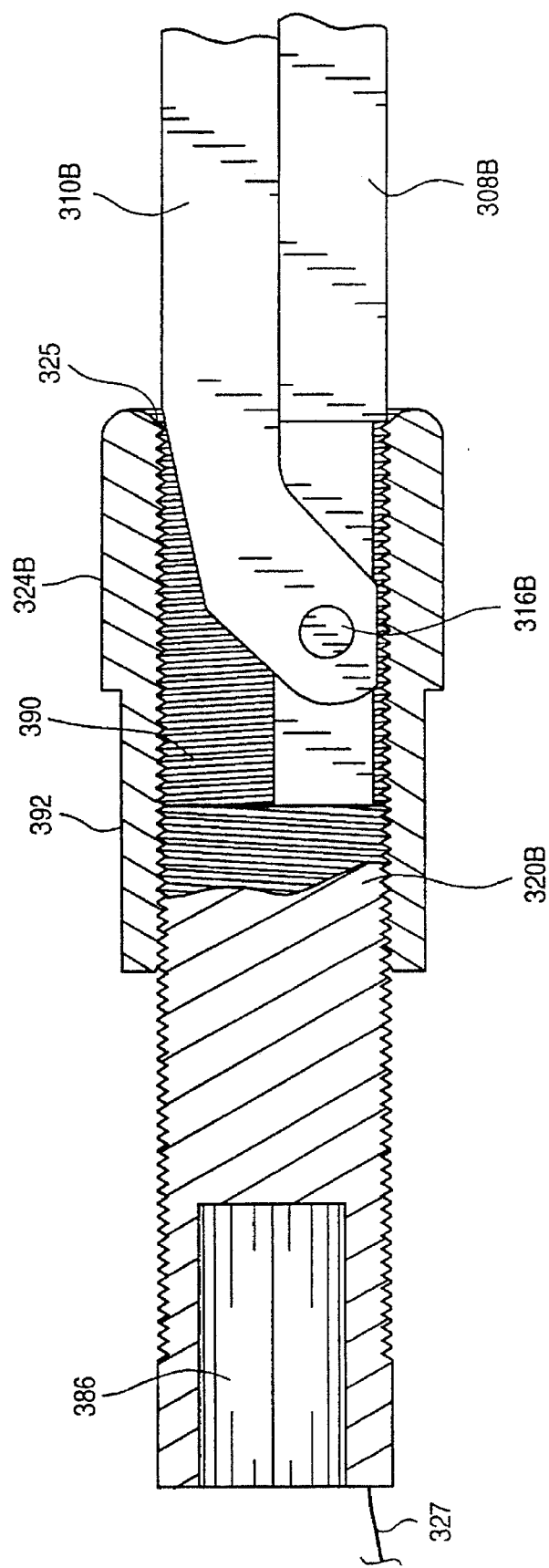

FIGS. 23 and 24 illustrate the use of a deployable clamping assembly 304A to clamp the aorta AO. The embodiments discussed below with reference to FIGS. 23–33A have like parts referred to with like reference numerals. A needle 50 penetrates the aorta for delivering cardioplegic fluid into the patient for paralyzing the myocardium. Alternatively, cardioplegic fluid may be delivered through a cannula positioned within the aorta as shown in FIG. 8. Clamp 304A has a pair of opposed jaws 308A, 310A pivotally mounted to one another at a pivot 367. Jaws 308A, 310A are maintained in the closed condition against the opening force of a compression spring 368 by the engagement by a pair of ratchets 370 mounted to jaw extensions 372, 374. The distal end of clamp positioner 306A has a pair of manipulator arms 350A, 352A which engage openings 376 in jaw extensions 372, 374 to close jaws 310A, 312A onto pulmonary artery PA. A tether 373 extends between the clamp 304A and the clamp positioner 306A so that the clamp 304A can be easily located after the clamp positioner 306A is removed from the patient. A separate device (not shown) can be used to disengage ratchets 370 to release jaws 308A, 310A so that the clamp positioner 306A can be used to remove the clamp 304A.

Clamp 304A is introduced through a trocar sleeve 348 in the closed position of FIG. 24. Clamp 304A and the portion of the clamp positioner 306A passing through trocar sleeve 348 are sized to fit within the trocar sleeve 348 which preferably has a maximum internal dimension of about 20 mm by 32 mm although any size may be provided. The size of trocar sleeve 348 is determined largely by the spacing between ribs R. The above described method may, of course, be performed using any of the clamps disclosed herein.

FIG. 25 illustrates a clamping assembly 302B having a clamp positioner 306B and a clamp 304B having first and second jaws 308B, 310B. The first jaw 310B is pivotally mounted to a threaded jaw extension 320B at a pivot 316B while jaw 308B is fixed. Jaws 308B, 310B are normally biased towards the open position of FIG. 27B by a torsion spring (not shown).

Clamp positioner 306B includes a hollow drive body 346B which houses a stabilizing rod 378. The hollow drive body 346B actuates the jaws while the stabilizing rod 378 stabilizes the clamp assembly against the torsional forces produced by rotational actuation of the rotatable drive body 346B. The actuator housing 324B includes a shoulder 325 against which the jaw 310B abuts due to the force of the torsion spring (not shown). Thus, slidable movement of the actuator housing 324B, and consequently shoulder 325, moves the jaws between the open and closed positions. The drive body 346B has a square opening 384 at the distal end which is configured to engage a square outer surface 392 of the jaw extension for rotatably driving the jaw extension 320B. The square opening 384 may have any other shape which is adapted for rotation. The jaw extension 320B has threads which engage the hollow actuator housing 324B so that rotation of the actuator housing 324B moves the actuator housing 324B relative to the jaws 308B, 310B. The stabilizing rod 378 has a square shaft 382 (FIG. 26) at a distal end which matingly engages a square hole 386 formed in the jaw extension 320B. The stabilizing rod 378 is coupled to a handle 380 for preventing rotation of the stabilizing rod 378. Although the handles 380, 394 are shown as discs, the handles 380, 394 may also be any other conventional hand grip.

A tether 327 is preferably attached to the clamp 304B at one end and extends through the drive body 346B. The tether 327 helps the user locate the clamp after the clamp positioner 304B is removed from the patient. A locking tab (not shown) is preferably provided at the handle 380 for locking the tether 327 to the handle 380. The tether 327 is preferably locked to the handle 380 so that the clamp 304B and clamp positioner 306B are coupled together when removing the clamp 304B from the patient. The tether 327 may be provided with any of the clamps described herein.

The clamp 304B is introduced into the thoracic cavity TC through a trocar sleeve 348 while in the closed position of FIG. 25. When clamp 304B is properly positioned, handle 380 is held stationary while the proximal end 394 of hollow drive body 346B is rotated thereby moving the actuator housing 324B and permitting jaws 308B, 310B to open. Once the aorta is properly positioned between jaws 308B, 310B, proximal end 394 of hollow drive body 346B is rotated in the opposite direction to close the jaws 308B, 310B. Once clamped onto the hollow structure, the clamp positioner 306B is preferably removed from the patient through trocar sleeve 348. When it is desired to remove the clamp, the tether 327 is used to locate the clamp and the clamp positioner 306B is used to remove the clamp 304B.

Figure 28A:
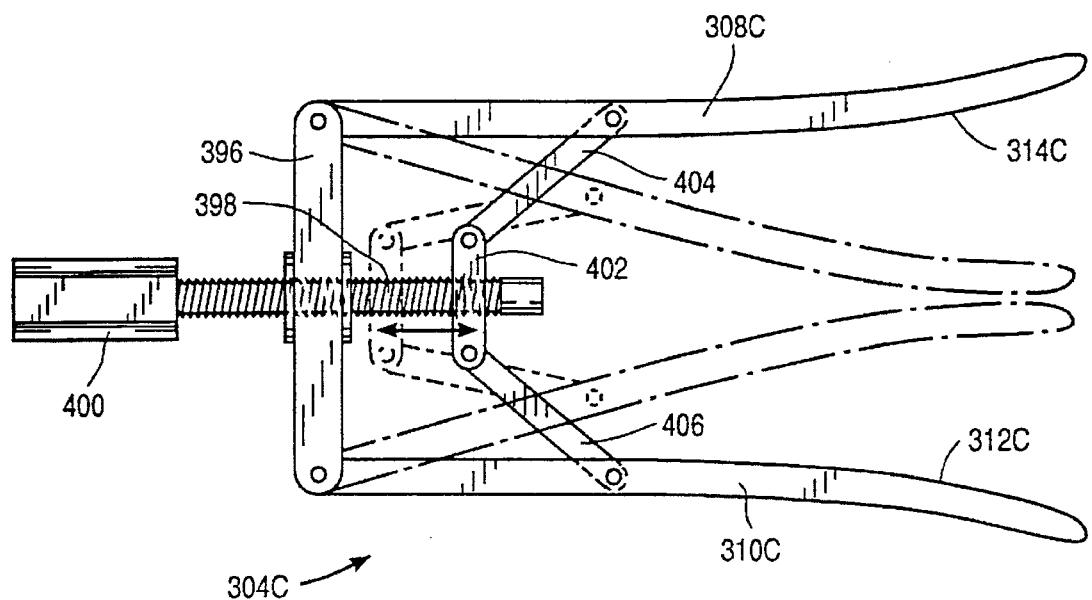
FIGS. 28A–C are plan, side and end views of another clamp.
Figure 28B:
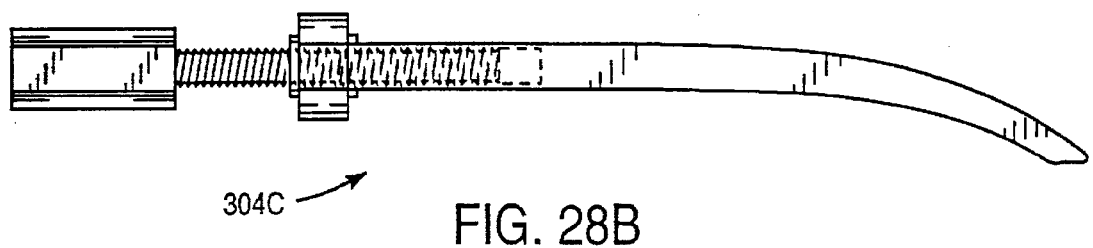
Figure 28C:
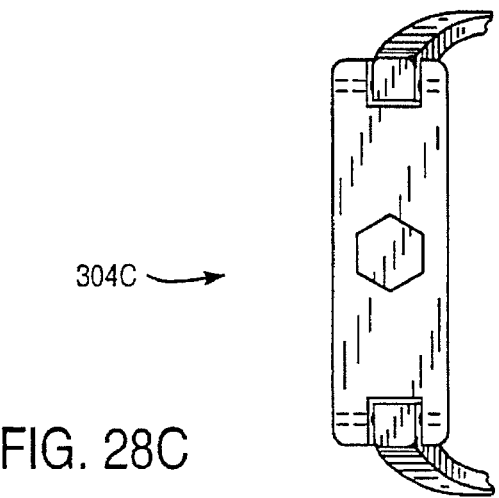

FIGS. 28A-28C show three different views of a clamp 304C which also uses a rotatable actuating element. Clamp 304C includes first and second jaws 308C, 310C having somewhat outwardly bowed jaw surfaces 312C, 314C so that they do not touch along their entire surfaces. Jaws 308C, 310C are also preferably curved when viewed from the side as shown in FIG. 28C Arms 308C, 310C are pivotally mounted to opposite ends of a clamp base 396. Clamp base 396 has a threaded central hole through which a threaded shaft 398 passes. The shaft 398 rotates within the threaded hole formed in base 396 so that rotation displaces the shaft axially relative to the base. A clamp positioner similar to that shown in FIG. 25 is preferably used to rotate a hex-head 400 while preventing base 396 from rotating. A connector 402 is coupled to a distal end of the shaft 398. Connector 402 is coupled to first and second jaws 308C, 310C by links 404, 406 so axial displacement of shaft 398 moves jaws 308C, 310C between the open, solid line position to the closed, dashed line position.

Figure 29A:
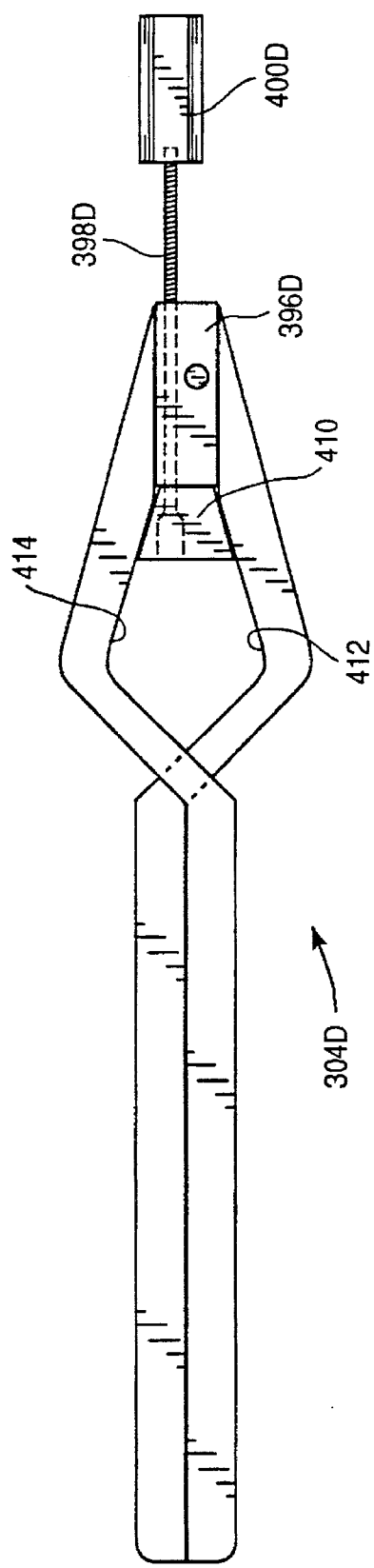
FIGS. 29A–B are side views of a further clamp in closed and opened positions.
Figure 29B:
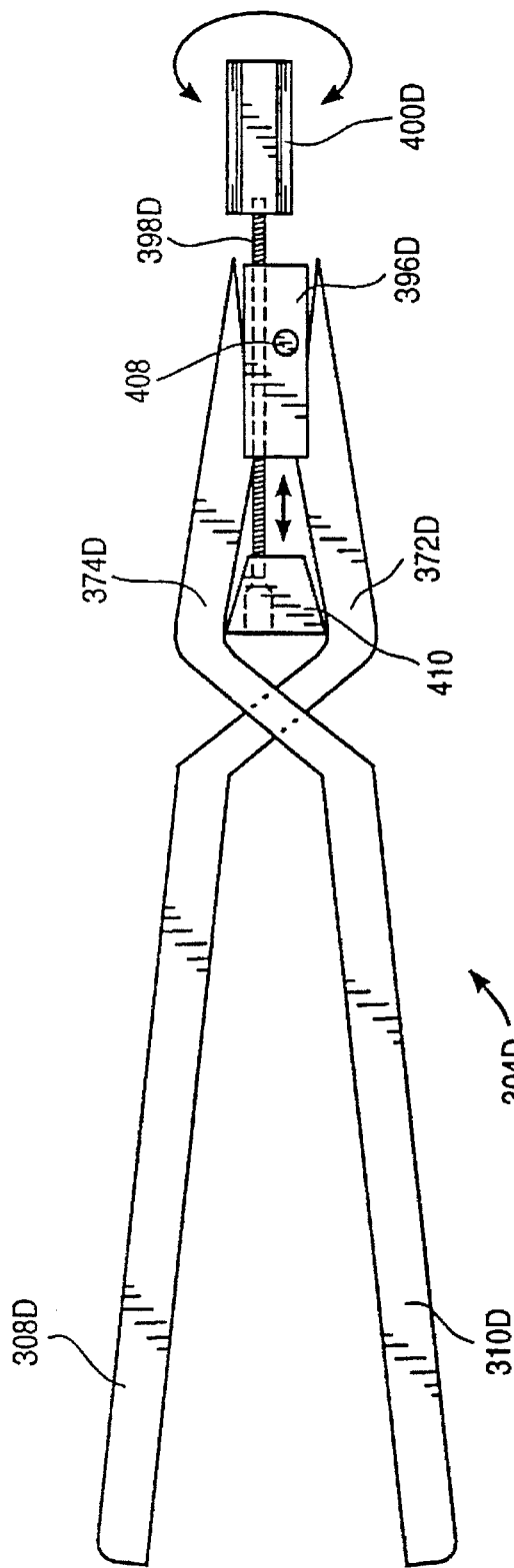

FIGS. 29A and 29B illustrate a clamp 304D having a pair of jaws 308D, 310D and jaw extensions 372D, 374D. The jaws 308D, 310D pivot about a pivot point 408 and are normally biased to the open position of FIG. 29B with a spring or any other conventional biasing mechanism, not shown. Clamp 304D includes a base 396D having a threaded bore through which a threaded shaft 398D passes. Threaded shaft 398D is connected to a wedge 410 at its outer end. Wedge 410 is sized to engage the opposed faces 412, 414 of extensions 372D, 374D for opening and closing the jaws 308D. Thus, rotating shaft 398D, while maintaining base 396D stationary, moves wedge 410 between the position of FIG. 29A, which closes jaws 308, 310, and the position of FIG. 29B, which opens jaws 308D.

FIGS. 30A-30C illustrate a clamping assembly 302E including a first jaw 308E having a jaw extension 320E housing the proximal end 416 of a second jaw 310E. Jaw 310E is pivotally mounted to jaw extension 320E at a pivot 418. A torsion spring 420 is mounted about pivot 418 which biases jaws 308, 310 to the open position of FIG. 30B. In the embodiment of FIGS. 30A-30C, jaw surfaces 312E, 314E are straight, atraumatic, toothed nesting surfaces commonly known as Debakey teeth. A pawl 342E is pivotally mounted to jaw 310E. Pawl 342E includes a number of teeth 340E which engage a stationary tooth 422 carried by jaw extension 320. Teeth 340E are biased towards tooth 422 by a torsion spring 424.

Clamp positioner 306B includes a first part 426 and a pair of second parts 428, 429 which slide relative to first part 426 in the direction of arrow 430. Part 426 has a hook 432 at its distal end which engages an eye 434 in jaw extension 320E. With clamp positioner 306E in the orientation of FIG. 30A and the hook 432 mounted in eye 434, the second part 428 is configured to engage the second jaw 310E. The second part 429 is moved in a distal direction to engage pawl 342E thereby pivoting pawl 342E away from tooth 422 and permitting jaw 310E to pivot to the open position of FIG. 30B.

The above-described embodiments of clamping assembly 302-302E all provide a clamp which is completely separable from the clamp positioner, apart from the tether, after being clamped onto a hollow body structure. Although it is preferred to provide a clamp positioner which is also used to retrieve the clamp after the medical procedure, it is within the scope of the present invention to provide a separate clamp remover which is used to remove the clamp after introduction with the clamp positioner. It also may be desired to provide the tether 327 to the clamp which extends through the trocar sleeve. Tether 327 does not take up much room and does not hinder access to the target region but aids retrieval of the clamp by guiding the distal end of the clamp positioner to the clamp when removing the clamp from the patient.

The following embodiments disclose jaw actuating mechanisms which include a cable or hydraulic actuator. An advantage of the cable and hydraulic actuators described below is that they also do not take up much room in the trocar sleeve and, therefore, enhance visualization and permit introduction of other instruments into the patient through the same trocar sleeve.

Referring to FIG. 31A, a clamping assembly 302F having a clamp 304F and a clamp positioner 306F is shown. Clamp 304F includes jaw surfaces 312F, 314F which are not parallel when the jaws are in the fully closed position of FIG. 31. The jaw surfaces 312F, 314F are covered with a resilient, ribbed material, having nesting troughs and grooves. This configuration may be useful when the hollow body structure being clamped has relatively thick walls (see FIG. 31E) so that when the hollow body structure is completely collapsed, jaws 308F, 310F will be generally parallel.

Clamp positioner 306F includes a coaxial cable 438 having an outer, hollow sheath 440 and an inner cable 442.

The distal end 444 of sheath 440 terminates at a recess 446 formed in jaw extension 372F. Cable 442 passes through jaw extension 372F and a compression spring 368F and is secured to the jaw extension 374F at ball end 448. Clamp positioner 306F includes a cable puller 450 having a distal end 452 against which a proximal end 454 of sheath 440 rests. Cable 442 passes through cable puller 450 and a second ball end 456 fits within a ball opening 458 on the handle 460. Handle 460 is secured to the base 462 of cable puller 450 at a pivot 464 and is biased to the position of FIG. 31A by the compression spring 466.

Coaxial cable 438 is preferably sufficiently rigid to enable the user to guide clamp 304F to the target location, often without the use of additional guiding structure, however, a guide rod or wire may also be used as disclosed below. Once clamp 304F is adjacent to the body structure to be clamped, handle 460 is pressed against base 462 thereby pulling cable 442 and opening the jaws 308F, 310F. The handle 460 is then released and spring 368F closes jaws 308F around the aorta. Ball end 456 may then be disengaged from ball opening 458 and sheath 440 can be removed from the patient through the trocar sleeve 348 while leaving cable 442 within the patient. In this manner, cable 442 serves as a tether permitting easy and rapid employment of cable sheath 440 against clamp 304F while taking up very little space within the trocar sleeve and creating minimal interference at the target region. Alternatively, the cable sheath 440 and cable 442 may remain in the patient. As discussed above, the trocar sheath through which the cable passes may include a passageway for holding the cable so that the cable is not inadvertently actuated by another instrument passing through the same trocar.

Referring to FIG. 31B, a clamp 304G including jaws 308G is shown. A torsion spring 468 biases the jaws 308G, 310G towards one another. The clamp 304G is substantially similar to the clamp 304F, however, the jaws 308G, 310G are not parallel when the jaws 308G, 310G are open.

Figure 31D:
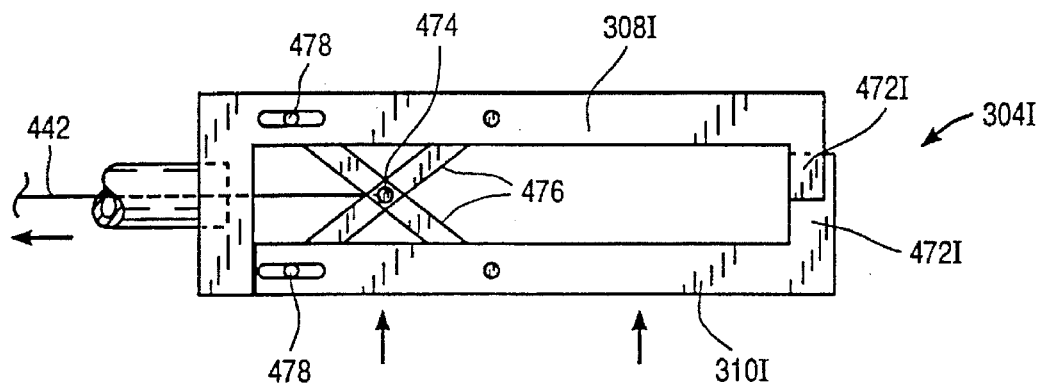
FIG. 31D illustrates an alternative embodiment of the clamp of FIG. 31C using a scissors mechanism to maintain the straight line movement of the jaws.

FIG. 31C shows a clamp 304H having jaws 308H, 310H which remain parallel throughout their movement. Jaw 308H includes a pair of slots 441 and jaw 310H includes a pair of pins 443 for maintaining the parallel relationship between jaws 308H, 310H. Clamp 304H includes a pair of inwardly directed tips 472 at the end of each jaw 308H, 310H. Tips 472 help retain the body part between the jaws 308H, 310H and also limit the maximum compression of the body part positioned therebetween. Compression spring 368H biases jaws 308H, 310H open so that pulling cable 442 closes jaws 308H, 310H. A toothed or ratcheted latch 470 locks the jaws 308H, 310H. Latch 470 is biased towards the latched position of FIG. 31B by a coil torsion spring, not shown. To release latch 470, sheath 440 includes an axially movable latch engagement element, not shown. Alternatively, a separate latch release mechanism may be provided FIG. 31D shows a clamp 304I having jaws 308I, 310I which move parallel to one another as in the embodiment of FIG. 31C. A cable 442 is attached to a central pivot 474 and a pair of links 476 so that pulling on cable 442 causes pivot 474 to move proximally thereby opening jaws 308I, 310I. The jaws 308I, 310I are biased closed by springs (not shown) coupled to the ends of links 476, 478. Clamp 304I also includes overlapping tissue-limiting tips which helps retain the body part between the jaws 308I, 310I and, furthermore, limits the overall compression of the body part. A safety spring or other tension-sensitive element could be used along cable 442 to limit the force exerted by the cable 442 for any of the cable actuated embodiments described herein.

Figure 31E:
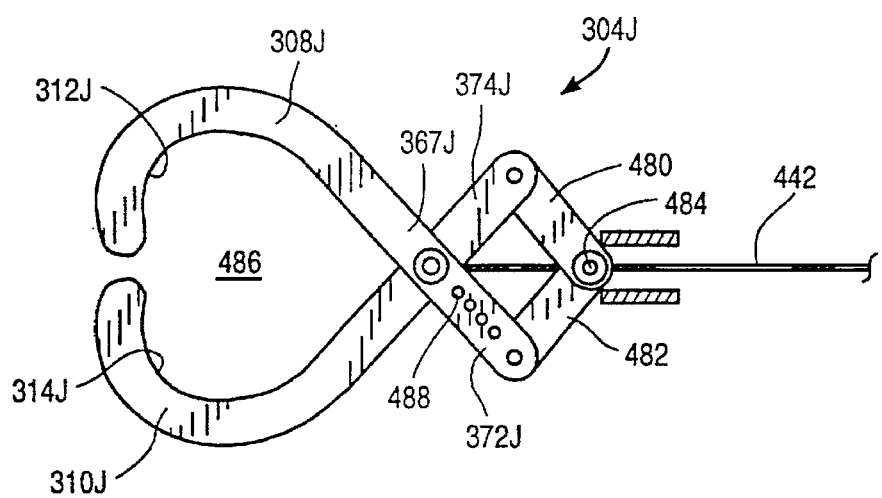
FIG. 31E illustrates another embodiment of the clamp of FIG. 31A using jaws with concave, opposed, atraumatic surfaces and a scissors-like opening and closing action.
Figure 31F:
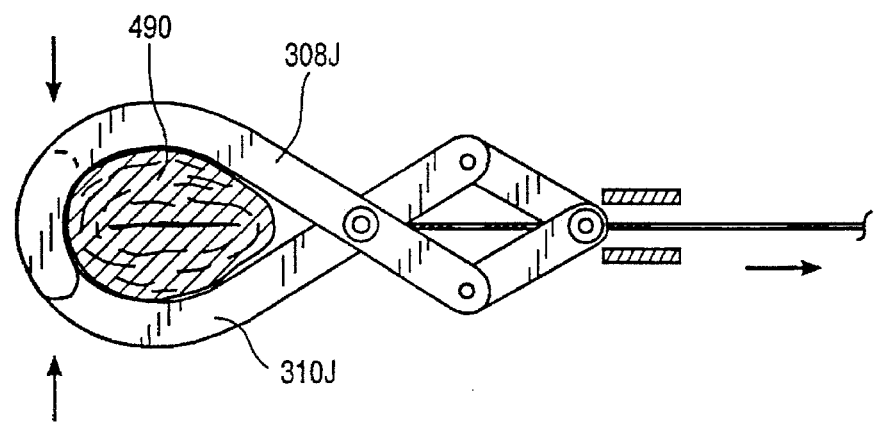
FIG. 31F illustrates a portion of the clamp of FIG. 31D providing a clamping force to a hollow body structure.

FIG. 31E illustrates a clamp 304J having a pair of concave jaws 308J, 310J coupled to one another at a pivot 367J. The proximal ends of jaw extensions 372J, 374J are connected to a pair of links 480, 482 with the links being coupled to one another at a common pivot 484. Cable 442 is coupled to pivot 367J so that pulling cable 442 causes pivots 367J and 484 to be drawn towards one another thereby opening jaws 308J, 310J. A torsion spring (not shown) is positioned at pivot 367J to bias jaws 308J, 310J closed. A minimum separation distance between the jaws 308J, 310J is defined by a set screw (not shown) positioned in one of the threaded openings 488. The set screw limits how far jaws 308J, 310J can be closed and the user selects the minimum separation distance between the jaws 308J by positioning the set screw in the appropriate threaded openings 488. FIG. 31F illustrates a relatively thick-walled hollow body structure 490, such as an aorta, captured between jaws 308J, 310J. As can be seen, the distal ends of the jaws overlap one another and help retain the hollow body structure between the jaws.

Figure 32A:
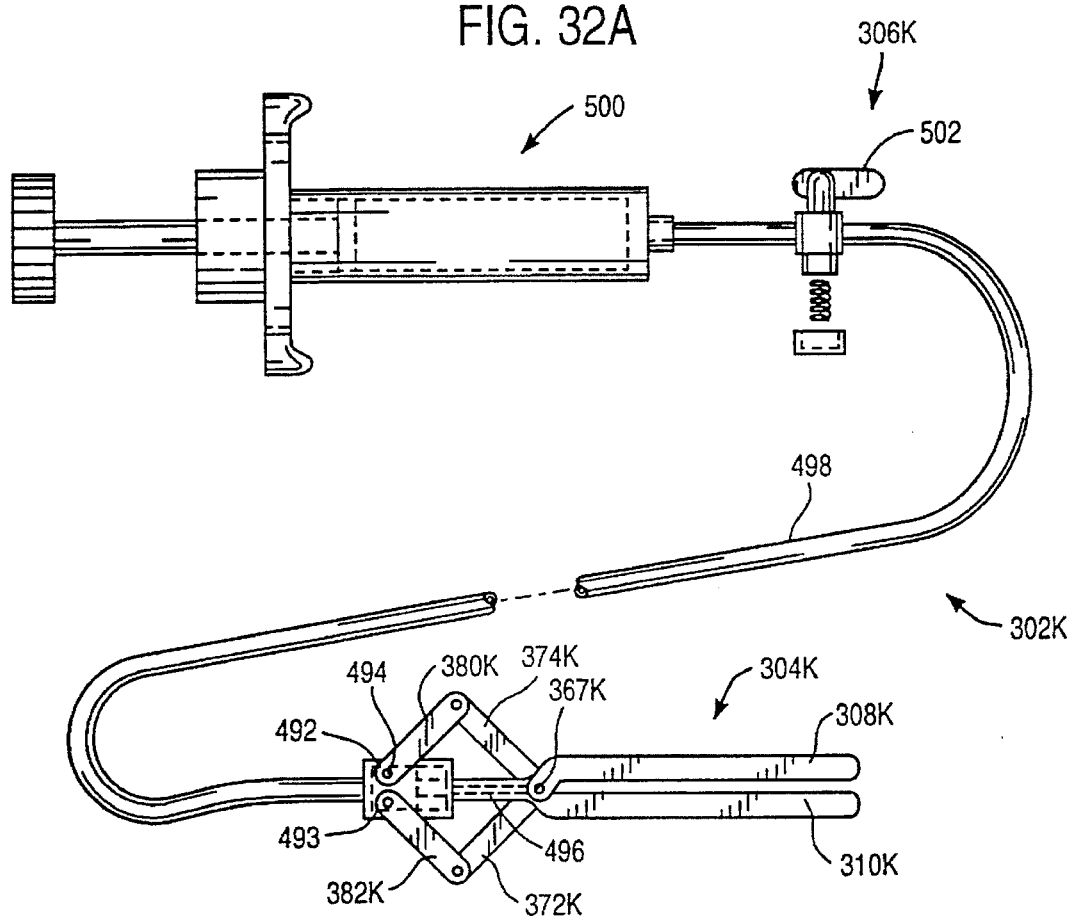
FIG. 32A illustrates a further clamping assembly using hydraulic pressure to actuate the clamp through a piston and cylinder arrangement.

FIG. 32A illustrates a clamp 304K actuated by a clamp positioner 306K having a hydraulic actuator. Links 380K, 382K are pivotally coupled to a cylinder 492 by pivots 494. Cylinder 492 houses a piston 493 coupled to a piston rod 496. The distal end of piston rod 496 is connected to pivot 367K so that movement of the piston rod causes jaws 308K, 310K to open and close. Cylinder 492 is supplied with hydraulic fluid through a hydraulic line 498. Clamp positioner 306K includes a syringe 500 which supplies hydraulic fluid to hydraulic fluid line 498 through pressure-relief shut-off valve 502. Although it is preferred to provide the syringe 500, any other hydraulic actuator may be provided. Valve 502 is closed when the desired pressure is applied to the cylinder 492. To prevent excessive force on the body part, valve 502 limits the pressure of the hydraulic fluid. If desired, the pressure relief feature of valve 502 could be adjusted according to the procedure being conducted, the condition of the patient and other pertinent information.

Figure 32B:
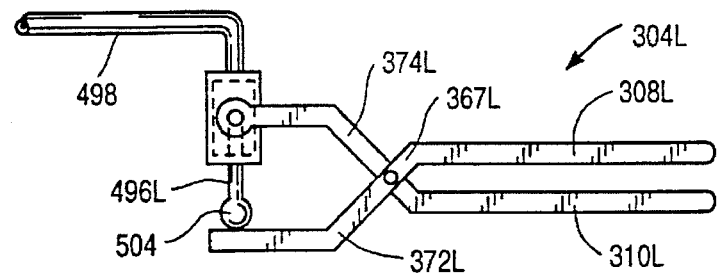
FIG. 32B illustrates an alternative embodiment of the clamp of FIG. 32A.

FIG. 32B shows a clamp 304L which is hydraulically actuated via hydraulic line 498 and hydraulic cylinder 492L. Application of hydraulic fluid through line 498 to cylinder 492L extends piston rod 496L so that a roller 504 presses against jaw extension 372L and closes jaws 308L, 310L. A torsion spring (not shown) can be used at pivot 367L and bias jaws 308L, 310L open.

Figures 33A, 33B:
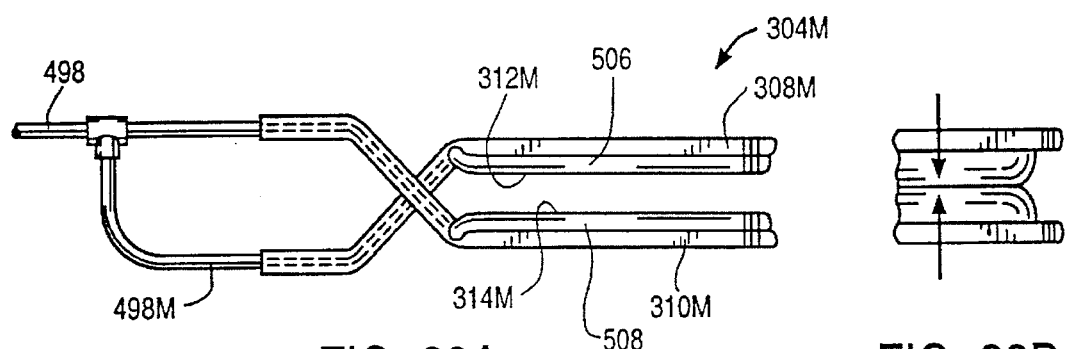
FIG. 33A shows a clamp having jaw surfaces defined by inflatable balloons.
FIG. 33B illustrates the distal ends of the jaws of FIG. 33 with the inflatable balloons inflated to close the opposed surfaces between the jaws.

FIG. 33A illustrates a clamp 304M including jaws 308M, 310M having jaw surfaces 312M, 314M defined by inflatable balloons 506, 508. The balloons 506, 508 are coupled to hydraulic lines 498, 498M for inflating the balloons. FIG. 33B illustrates the balloons 506, 508 in an expanded, clamped position.

Figure 34:
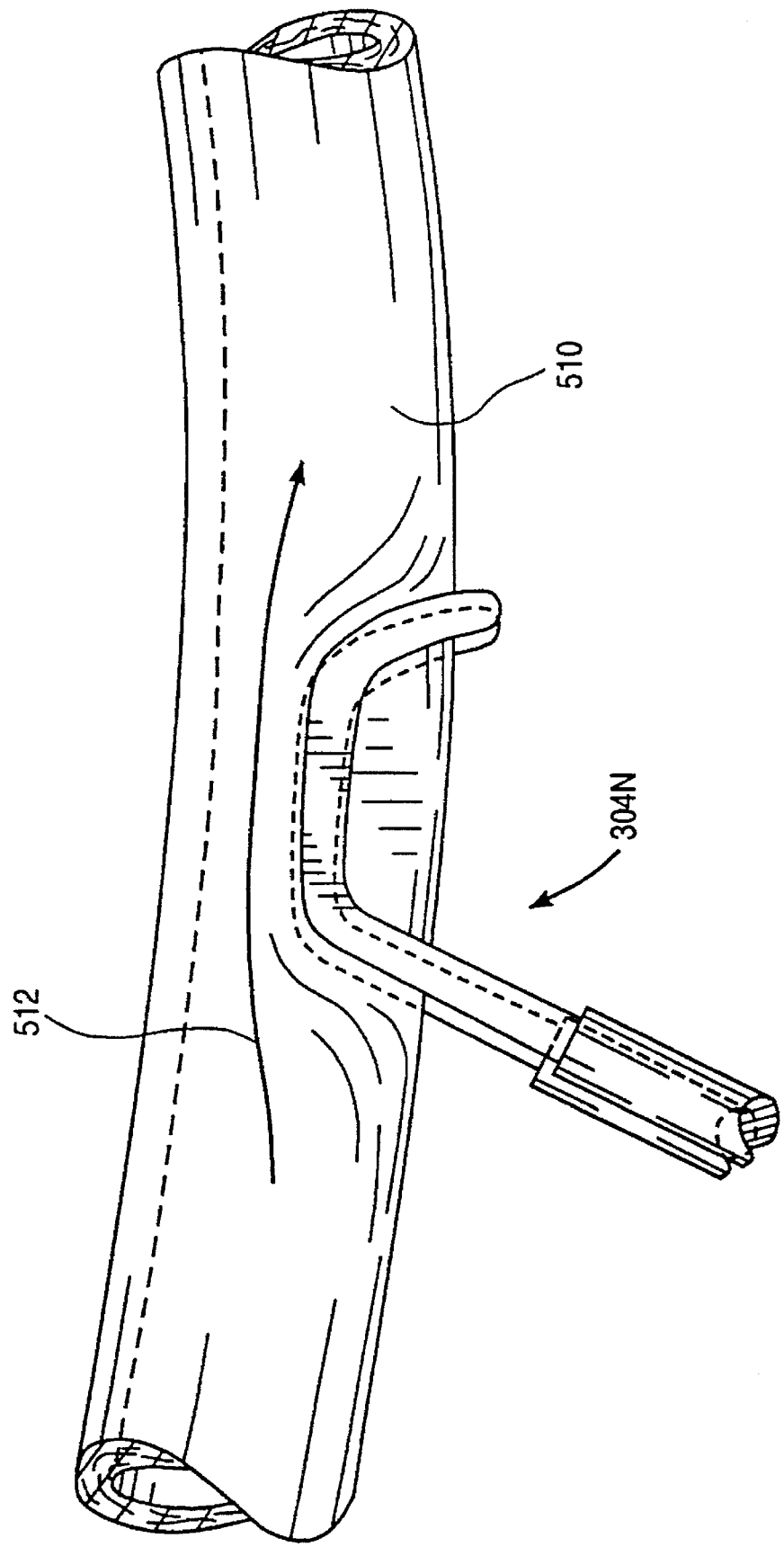
FIG. 34 is a simplified view showing a side biting clamp clamping onto a blood vessel.

FIG. 34 illustrates a side-biting clamp 304N clamping onto a blood vessel 510 in a manner to restrict but not prevent fluid flow through the blood vessel as suggested by arrow 512. Although all of the previous embodiments have been described in connection with occluding the clamped body structure, all of the clamps disclosed herein may also be used to partially occlude the body structure in a manner similar to the clamp 304N of FIG. 34.

Figure 35:
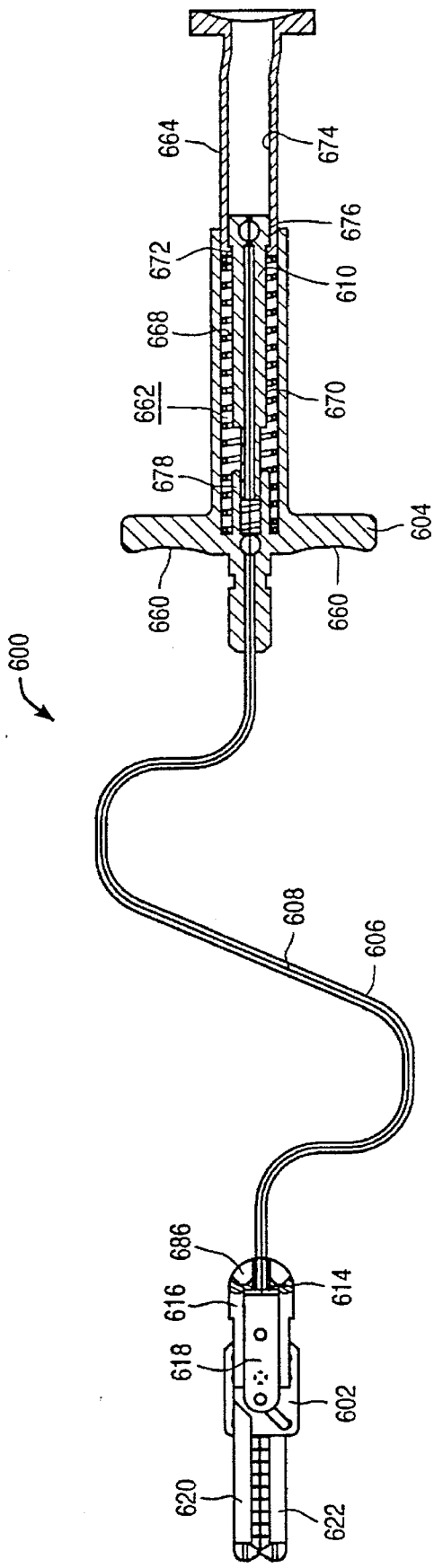
FIG. 35 shows a clamp assembly with the proximal end having a handle in cross-section and the distal end having a clamp in partial cross-section.

Referring to FIG. 35, a clamp assembly 600 is shown which includes a clamp 602 and a handle 604. The handle 604 and a portion of the clamp 602 are shown in cross-section. A cable 606 and a sheath 608 extend between the clamp 602 and handle 604. The cable 606 is housed within the sheath 608 and is connected to a cable puller 610. The cable 606 is used for actuating the clamp 602 as described below. The sheath 608 is held at a first sheath holder 612 at the handle 604 and at a second sheath holder 614 at an anchor 616. The cable 606 passes through the anchor 616 and is coupled to a slide 618 which is slidably coupled to the anchor 616. The sheath 608 and cable 606 preferably has a length from the distal end of the handle to the proximal end of the clamp which is at least 6 inches, and more preferably at least 10 inches, so that the clamp can reach the internal mammary artery through an percutaneous intercostal penetration while the handle remains outside the patient's chest. The slide 618 and anchor 616 will also be described in greater detail below. The cable 606 preferably has a 0.018 inch outer diameter and is made of stainless steel. The sheath 608 is preferably a 0.050 inch outer diameter coil spring made of stainless steel. A 0.0005 shrink tube made of polyester is placed over the coil spring to prevent stretching. Any other cable and sheath may be used without departing from the scope of the invention. The sheath 610 and cable 606 advantageously permit the introduction of other instruments through the same instrument delivery member since the sheath 610 takes up little room in the instrument delivery member and can be moved to a convenient location which does not hinder access of other instruments through the same instrument delivery member. The sheath 610 preferably has a maximum outer diameter of less than 0.080, and more preferably equal to or less than 0.050.

The clamp 602 includes a first jaw 620 and a second jaw 622. The first and second jaws 620, 622 each include a jaw member 624 having an atraumatic jaw surface 626. The jaws 620, 622 are movable between the closed position of FIG. 35 and the open position of FIG. 39. Although it is preferred that both jaws 620, 622 be movable between the open and closed positions, the clamp 602 may also be configured with only the first jaw 620 being movable. Referring to FIGS. 40 and 41, side views of the first and second jaws 620, 622 are shown with the second jaw 622 having the jaw member 624 attached. The jaws 620, 622 includes first, second and third slots 628, 630, 632 with the second slot 630 being oriented substantially perpendicular to the jaw surfaces 626. The second slot 630 of the first and second jaws 620, 622 are aligned so that a pin passing through the second slots 630 helps maintain the first and second jaw surfaces 626 parallel to one another throughout movement between the open and closed positions. The first and third slots 628, 632 of each of the jaws 620, 622 are parallel to one another and oriented 45 (degrees) relative to the jaw surface 626. Referring to FIG. 35, first, second and third pins 629, 631, 633 pass through the first, second and third slots 628, 630, 632.

Referring to the plan view of FIG. 42, the jaws 620, 622 each include a T-shaped slot 634 for attaching the jaw members 624 to the jaws 620, 622. The slots 634 include a detent 636 which engages a protrusion 639 (FIG. 43) in the jaw members 624 for securing the jaw member 624 to the jaws 620, 622. The jaws 620, 622 also include side surfaces 636 which engage one another throughout movement between the open and closed positions. Referring to FIG. 43, the jaw member 624 has a retention tooth 638 at the distal end which extends beyond the jaw surface 626. The retention teeth 638 help retain a clamped body structure between the jaws 620, 622 even when the jaws 620, 622 are slightly open as shown in FIG. 38. The jaw member 624 also has a rounded bumper 640 at the distal end for minimizing trauma to the patient when the clamp 602 is introduced into the body. The jaw member 624 advantageously provides the atraumatic jaw surface 626, bumper 640 and retention tooth 638 in an integral piece which is easily attached to the first and second jaws 620, 622. The jaws 620, 622 surfaces also include ribs 635 which also help retain a clamped body structure between the jaws 620, 622.

Referring to FIG. 44, an enlarged cross-sectional view of the jaws 620, 622 and jaw members 624 is shown. The retention teeth 638 are preferably offset so that the retention teeth 638 do not interfere with one another when the jaws 620, 622 are closed. The jaw members 624 are preferably hollow to further cushion the clamped body structure. The jaw members 624 are preferably made of silicone but may be formed of any other suitable material.

Referring to FIGS. 45 and 46, side and plan views of the slide 618 are shown. The slide 618 includes a throughhole 642 for receiving the cable 606. The distal end of the cable 606 preferably has an anchor (not shown) which prevents withdrawal of the cable 606 through the throughhole 642. The slide 618 includes first and second holes 644, 646 extending through first and second sides 648, 650. The first and third pins 629, 633 extend through the first and second holes 644, 646 and the first and third slots 628, 632 of the first and second jaws 620, 622 for moving the first and second jaws 620, 622 when the slide 618 is moved. The slide 618 also includes grooves 652 extending between the first and second holes 644, 646.

Referring to FIGS. 47 and 48, side and plan views of the anchor 616 are shown. The anchor 614 includes central guides 654 which are positioned in the grooves 652 of the slide 618. The central guides 654 and grooves 652 cooperate to help maintain the linearly slidable relationship between the slide 618 and anchor 614. The central guides 654 also include holes 656 therethrough for receiving the second pin 631 which extends through the second slots 630 in the first and second jaws 620, 622. The anchor 614 has a rounded proximal end 658 which facilitates withdrawal of the clamp 602 from the patient. The proximal end 658 also has the second sheath holder 614 for receiving the sheath 606. The anchor 614 also includes four arms 615, three of which are shown in FIGS. 47 and 48, which extend between the central guides 654 and the proximal end 658.

Referring again to FIG. 35, the handle 604 includes a pair of finger engaging elements 660 positioned on opposite sides of a cavity 662. An actuator 664 is slidably disposed within the cavity 662 for actuating the first and second jaws 620, 622. The actuator 664 is positioned between the finger engaging elements 660 for easy manipulation with the thumb or palm of the hand. Although it is preferred to provide the finger engaging elements 660 and centrally located actuator 664, the handle 604 may have any other configuration such as a pistol-type handle with a trigger actuator.

A spring 668 is positioned within the cavity 662 with the cable 606 extending through the spring 668. The spring 668 provides a biasing force between the cable 606 and the handle 604 for biasing the jaws 620, 622 toward the closed position. The cable puller 610 has a threaded exterior surface 670 which matingly engages a threaded interior surface 672 of the actuator 664. Alternatively, the interior surface 674 of the actuator 664 may be threadably coupled to the exterior surface 676 of the cable puller 610. The handle 604 also includes a guide 678 which receives the cable puller 610. The guide 678 preferably has a square internal cross-sectional shape (not shown) and the cable puller 610 has a correspondingly sized square external cross-sectional shape (not shown) so that the cable puller 610 does not rotate within the cavity 662.

The spring force which biases the jaws 620, 622 toward the closed position is varied by changing the position of the actuator 664 thereby changing the compression of the spring 668. Referring to FIGS. 35 and 37, rotation of the actuator 664 moves the actuator 664 relative to the cable puller 610 and the handle 604. The clamping force of the clamp assembly 600 in FIG. 35 is low since the spring 668 is relaxed while the clamping force of the clamp assembly in FIG. 37 is high since the spring 668 is compressed. Although it is preferred to threadably couple the cable puller 610 and actuator 664 together, the cable puller 610 may be coupled to the actuator 664 and handle 604 in any other manner. For example the cable puller 610 may be rotatably coupled to the handle 604, the actuator may be linearly stable on the cable puller, and/or the spring 668 may be a torsion spring or a cantilevered lever instead of a compression spring.

Figure 36:
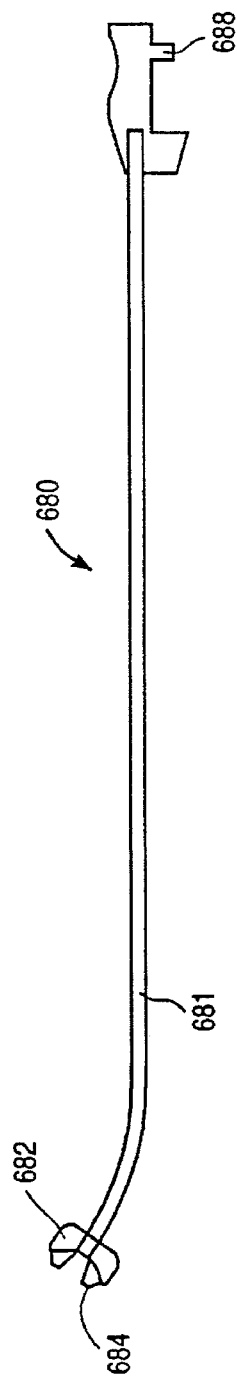
FIG. 36 shows an introducer for introducing the clamp of FIG. 35 into a patient.

Referring to FIG. 36, the clamp assembly preferably includes an introducer 680 for facilitating introduction of the clamp 602 into the patient. The introducer 680 has a clamp holder 682 which is releasably fixed to the clamp 602. The introducer 680 has a pair of prongs 684 which engage a pair of holes 686 in the clamp 602. The proximal end of the introducer 680 has a rib 688 which engages a slot 690 in the handle 604. The introducer 680 also has a malleable shaft 681 which can be bent to a desired shape. Although it is preferred to releasably couple the introducer 680 to the handle 604, the introducer 680 may be completely independent of the handle 604. Referring to FIG. 49, the introducer 680 has a length similar to the length of the clamp assembly 600 so that the sheath 610 is pulled taught when the introducer 680 is coupled to the clamp 602 and handle 604. In this manner, the introducer 680 retains the clamp 602 with the prongs 684. To release the clamp 602, the rib 688 is disengaged from the slot 690 and the introducer 680 is simply pulled from the clamp 602 with the prongs 684 sliding out of the holes 686. The introducer 680 may also include an actuator for positively attaching and releasing the clamp 602 to and from the clamp holder 682. Although it is preferred to provide the introducer 680, the clamp 602 may also be positioned with a conventional medical instrument such as forceps or the like.

Referring to FIG. 50, the clamp assembly 600 also preferably includes an indicator 692 which provides a relative indication of the spring 668 compression. The indicator 692 extend through a slot 694 in the handle 604 and a numerical scale indicates the relative clamping force. Referring to FIG. 51, the indicator 692 is received in a circumferential slot 696 in the distal end of the actuator 664. When the actuator 664 is rotated, the indicator 692 translates in the slot 696. The clamp assembly 600 also preferably includes a clip 698 for securing the handle 604 to a drape or curtain which covers the patient.

Referring to FIGS. 35, 37, 39 and 49, operation of the clamp 602 is now described in connection with clamping an internal mammary artery. Although clamping of the internal mammary artery is described as a preferred use of the clamping assembly, the clamp assembly may, of course, be used for clamping any other body structure. When the jaws 620, 622 are in the closed position of FIGS. 35, the slide 618 is biased toward the proximal end by the spring 668 and is positioned near the proximal end of the anchor 614. If a high clamping force is desired, the actuator 664 is rotated to the position of FIG. 37. If a low clamping force is desired, the actuator 664 is moved to the position of FIG. 35. The clamp 602 is then mounted to the introducer 680 as shown in FIG. 49 and the clamp 602 is introduced into the patient. When the clamp 602 is positioned near the internal mammary artery, the actuator 664 is depressed so that the cable 606 and slide 618 move distally relative to the sheath 610. The pin and slot configuration of the jaws 620, 622, slide 618 and anchor 614 cause the jaws 620, 622 to move to the open position while moving parallel to one another as shown in FIG. 39. The clamp 602 is then moved so that the internal mammary artery is positioned between the jaws 620, 622. The actuator 664 is then released so that the jaws 620, 622 close around the internal mammary artery. The rib 688 of the introducer 680 is released from the handle 604 and the introducer 680 is pulled from the clamp 602 and removed from the patient. The handle 604 is then moved to a convenient location where it will not interfere with the medical procedure such as grafting of the internal mammary artery to a blocked coronary artery. After the procedure is completed, the actuator 664 is depressed to open the jaws 620, 622 and the clamp 602 is then simply pulled from the patient. An advantage of the clamp assembly 600 is that the clamping force may be adjusted during the procedure without requiring re-application of the clamp 602. If, for example, the clamped body structure is a blood vessel which is not fully occluded, the clamping force may be increased without releasing the clamp 602. Referring to FIG. 38, another advantage of the clamp assembly is that the retention teeth 638 can be used to retain the body structure even when the jaws 620, 622 are separated. After the internal mammary artery is grafted to a downstream portion of an occluded coronary artery, the actuator 664 is depressed to release the clamp 602 and permit blood flow through the internal mammary artery.

The clamp assembly 600 advantageously provides a clamp 602 which may be actuated at a location remote from the clamp 602 and is particularly useful for temporarily clamping a body structure such as an internal mammary artery. The clamp 602 may be positioned around the internal mammary artery with the cable 606 and sheath 610 extending through an instrument delivery member such as a trocar, cannula, retractor, or the like. Although it is preferred to provide the pin and slot configuration of the FIGS. 35, it is also within the scope of the present invention to use any of the other cable actuated clamps described above with the actuator 664. Conversely, any of the actuators described above may be used with the clamp 602 of FIG. 35.

While the clamps described have been described specifically with reference to aortic clamping and clamping of the internal mammary artery, it will be understood to those of ordinary skill in the art that the invention is useful in a variety of other interventional procedures as well. For example, the clamping device of the invention may be used for clamping, cannulation of, and infusing fluid into blood vessels other than the aorta, as well as hollow body structures such as the bowel, bile duct, colon, and various other tubular ducts and organs. Furthermore, all of the clamps are suited for the procedures described herein including use of the intraluminally positionable delivery cannula 172 shown in FIGS. 7, 8, and 10–14 and the tether of FIGS. 23–25. In addition, although each of the preferred jaw shapes may be described with a particular actuating mechanism, any jaw shape may be used with the clamps and actuating mechanisms described herein and, in particular, curved and flattened tips will aid in blunt dissection. While the above is a complete description of the preferred embodiments of the invention, various alternatives, modifications and equivalents may be used. Therefore, the above description should not be taken as limiting the scope of the invention, which is defined by the claims.

What is claimed is:

1. A method of clamping a structure in a patient, comprising the steps of:

providing a clamp, a cable puller, a flexible sheath, and a flexible cable, the handle having a first sheath holder and the clamp having a second sheath holder, the sheath extending between the first and second sheath holders, the cable being at least partially housed within the sheath and generally conforming to a shape of the sheath, the cable also being coupled to the cable puller and the cable puller being adapted to displace the cable relative to the sheath, the clamp having a first jaw and a second jaw, the first jaw being movable relative to the second jaw between an open position and a closed position, the first jaw being coupled to the cable so that the first jaw moves between the open and closed positions when the cable is moved by the cable puller, the first and second jaws having atraumatic contact surfaces, the flexible sheath and flexible cable being deformable so that the cable puller can move the cable relative to the sheath when the flexible sheath is curved;

introducing the clamp into a patient;

moving the cable puller thereby displacing the cable relative to the sheath and moving the first jaw to the open position;

positioning the body structure of a patient between the first and second jaws after the moving step;

clamping the body structure by moving the cable puller thereby closing the jaws around the body structure; and moving the first and second jaws to the open position and unclamping the body structure, the atraumatic contact surfaces of the first and second jaws being configured to minimize damage to the body structure thereby leaving the body structure substantially in tact.

2. The method of claim 1, wherein:

the providing step is carried out with an introducer releasably coupled to the clamp; and the positioning step is carried out by manipulating the introducer so that the first and second jaws are positioned around the body structure.

3. The method of claim 2, further comprising the step of:

disengaging the introducer from the clamp after the positioning step.

4. The method of claim 1, wherein:

the providing step is carried out with both the first and second jaws being movable between the open and closed positions.

5. The method of claim 1, further comprising the step of:

adjusting a force biasing the first and second jaws toward the closed position.

6. The method of claim 1, wherein:

the providing step is carried out so that the first and second jaws move substantially parallel to one another when moving from the open position to the closed position.

7. The method of claim 1, wherein:

the providing step is carried out with the contact surfaces comprising an elastomeric material.

8. The method of claim 1, further comprising the steps of:

holding the clamp with an introduction device during the positioning step; and releasing the clamp from the introduction device after the clamping step.

9. A method of clamping a structure in a patient, comprising the steps of:

providing a clamp, a cable puller, a flexible sheath, and a flexible cable, the handle having a first sheath holder and the clamp having a second sheath holder, the sheath extending between the first and second sheath holders, the cable being at least partially housed within the sheath and being coupled to the cable puller, the cable puller being adapted to displace the cable relative to the sheath, the clamp having a first jaw and a second jaw, the first jaw being movable relative to the second jaw between an open position and a closed position, the first jaw being coupled to the cable so that the first jaw moves between open and closed positions when the cable is moved by the cable puller;

introducing the clamp into a patient;

moving the cable puller thereby displacing the cable relative to the sheath and moving the first jaw to the open position; and positioning a body structure of a patient between the first and second jaws after the moving step; and closing the jaws around the body structure by moving the cable puller;

the providing step being carried out with both the first and second jaws being movable between the open and closed positions;

the moving step being carried out with the first and second jaws having jaw surfaces remaining substantially parallel to one another when moving between the open and closed positions.

10. A method of clamping a structure in a patient, comprising the steps of:

providing a clamp, a cable puller, a flexible sheath, and a flexible cable, the handle having a first sheath holder and the clamp having a second sheath holder, the sheath extending between the first and second sheath holders, the cable being at least partially housed within the sheath and being coupled to the cable puller, the cable puller being adapted to displace the cable relative to the sheath, the clamp having a first jaw and a second jaw, the first jaw being movable relative to the second jaw between an open position and a closed position, the first jaw being coupled to the cable so that the first jaw moves between the open and closed positions when the cable is moved by the cable puller;

introducing the clamp into a patient;

moving the cable puller thereby displacing the cable relative to the sheath and moving the first jaw to the open position;

positioning a body structure of a patient between the first and second jaws after the moving step; and closing the jaws around the body structure by moving the cable puller;

the positioning step being carried out with the body structure being an internal mammary artery.

11. A clamp for clamping a body structure in a patient, comprising:

a handle having a first sheath holder;

a clamp having a second sheath holder, a cable holder, a first jaw and a second jaw, the first jaw being movable relative to the second jaw between an open position and a closed position, at least the first jaw being operably coupled to the cable holder for moving the first jaw between the open and closed positions;

a flexible sheath extending between the first and second sheath holders;

a flexible cable at least partially housed within the sheath and generally conforming to a shape of the sheath;

a spring biasing the cable relative to the sheath, the spring biasing the first and second jaws toward the closed position; and a cable puller movably coupled to the handle, the cable puller being configured to displace the cable relative to the sheath when the flexible sheath is curved.

12. The clamp of claim 11, wherein:
the second jaw is also movable between the open and closed positions relative to the first jaw.

13. The clamp of claim 12, wherein:
the first and second jaws remain substantially parallel to one another when moving between the open and closed positions.

14. The clamp of claim 11, wherein:
at least one of the cable and the cable puller extends at least partially through the spring.

15. The clamp of claim 11, further comprising:
a manually operable actuator movably coupled to the cable puller.

16. The clamp of claim 11, wherein:
the cable puller is slidable relative to the handle.

17. The clamp of claim 11, further comprising:
a first pin;
a second pin;
the first and second jaws each including a first slot, the first pin passing through the first slot in each of the first and second jaws;
the first and second jaws each including a second slot, the second pin passing through the second slot in each of the first and second jaws;
the first and second slots of each of the first and second jaws being parallel to one another.

18. The clamp of claim 11, wherein:
the handle includes first and second finger engaging members positioned on opposite sides of a proximal end of the cable and sheath.

19. The clamp of claim 11, wherein:
the first and second jaws each include a jaw member having a rounded bumper at a distal tip so that trauma to a patient is minimized during insertion of the clamp.

20. The clamp of claim 19, wherein:
the jaw member includes an atraumatic jaw surface integrally formed with the bumper.

21. The clamp of claim 11, further comprising:
a spring force adjusting member contacting the spring and being coupled to the cable puller, the spring force adjusting member being configured to adjust a closing force of the first and second jaws.

22. The device of claim 11, wherein:
the first and second jaws have atraumatic contact surfaces.

23. The device of claim 11, wherein:
the first and second jaws remain substantially parallel to one another when moving from the open position to the closed position.

24. The clamp of claim 11, wherein:
the cable puller is linearly slidable relative to the handle;
the handle having means for preventing rotation of the cable puller.

25. The clamp of claim 11, further comprising:
first and second links coupled to one another at a first pivot, the first and second jaws being coupled to one another at a second pivot;
the cable being coupled to at least one of the first and second pivots for moving the first jaw from the open position to the closed position.

26. A clamp for clamping a body structure in a patient, comprising:

a handle having a first sheath holder;
a clamp having a second sheath holder, a cable holder, a first jaw and a second jaw, the first jaw being movable relative to the second jaw between an open position and a closed position, at least the first jaw being operably coupled to the cable holder for moving the first jaw between the open and closed positions;
a flexible sheath extending between the first and second sheath holders;
a flexible cable at least partially housed within the sheath; and
a cable puller movably coupled to the handle, the cable puller being configured to displace the cable relative to the sheath;
the cable including an end which is detachable from the clamp.

27. A clamp for clamping a body structure in a patient, comprising:
a handle having a first sheath holder;
a clamp having a second sheath holder, a cable holder, a first jaw and a second jaw, the first jaw being movable relative to the second jaw between an open position and a closed position, at least the first jaw being operably coupled to the cable holder for moving the first jaw between the open and closed positions;
a flexible sheath extending between the first and second sheath holders;
a flexible cable at least partially housed within the sheath;
a cable puller movably coupled to the handle, the cable puller being configured to displace the cable relative to the sheath;
a spring biasing the cable relative to the sheath, the spring biasing the first and second jaws toward the closed position;
a spring force adjusting member contacting the spring and being coupled to the cable puller, the spring force adjusting member being configured to adjust a closing force of the first and second jaws; and
an actuator movably coupled to the handle, the actuator being connected to the cable puller and contacting the spring, the actuator being movable relative to the handle between a first position, in which a first clamping force is applied to the actuator by the spring when the jaws are in the closed position, and a second position, in which a second clamping force is applied by the spring when the first and second jaws are in the closed position, the first clamping force being larger than the second clamping force.

28. A clamp, comprising:
a clamp body having a distal end; and
a jaw member coupled to the clamp body, the jaw member having an atraumatic jaw surface and a bumper, the bumper extending substantially around a distal end for reducing trauma when the clamp is inserted into a patient, the bumper being integrally formed with the atraumatic jaw surface;
the jaw member including a retention member extending from the atraumatic surface at the distal end of the clamp body, the retention member being integrally formed with the atraumatic jaw surface and the bumper.

29. A clamp for clamping a body structure in a patient, comprising:
a handle having a first sheath holder;
a clamp having a second sheath holder, a cable holder, a first jaw and a second jaw, the first jaw being movable relative to the second jaw between an open position and a closed position, at least the first jaw being operably coupled to the cable holder for moving the first jaw between the open and closed positions, the first and second jaws remaining substantially parallel to one another when moving from the open position to the closed position;

a flexible sheath extending between the first and second sheath holders;

a flexible cable at least partially housed within the sheath and generally conforming to a shape of the sheath; and a cable puller movably coupled to the handle, the cable puller being configured to displace the cable relative to the sheath when the flexible sheath is curved.

30. The device of claim 29, wherein:

the first and second jaws have atraumatic contact surfaces.

31. A clamp for clamping a body structure in a patient, comprising:

a handle having a first sheath holder;

a clamp having a second sheath holder, a cable holder, a first jaw and a second jaw, the first jaw being movable relative to the second jaw between an open position and a closed position, at least the first jaw being operably coupled to the cable holder for moving the first jaw between the open and closed positions;

a flexible sheath extending between the first and second sheath holders;

a flexible cable at least partially housed within the sheath;

a cable puller movably coupled to the handle, the cable puller being configured to displace the cable relative to the sheath; and an introducer releasably attached to the clamp.

32. The clamp of claim 31, wherein:

the introducer is releasably attached to the handle.

33. The clamp of claim 31, wherein:

the introducer is malleable so that the introducer may be deformed.

\* \* \* \* \*